United States Patent
Augustine et al.

(10) Patent No.: US 7,837,721 B2
(45) Date of Patent: Nov. 23, 2010

(54) PATIENT COMFORT APPARATUS AND SYSTEM

(75) Inventors: Scott D. Augustine, Bloomington, MN (US); Thomas Peter Anderson, Savage, MN (US); Randall Charles Arnold, Minnetonka, MN (US)

(73) Assignee: Arizant Healthcare Inc., Eden Prarie, MN (US)

( * ) Notice: Subject to any disclaimer, the term of this patent is extended or adjusted under 35 U.S.C. 154(b) by 1427 days.

(21) Appl. No.: 10/508,319

(22) PCT Filed: Apr. 10, 2003

(86) PCT No.: PCT/US03/11128

§ 371 (c)(1),
(2), (4) Date: Mar. 3, 2005

(87) PCT Pub. No.: WO03/086500

PCT Pub. Date: Oct. 23, 2003

(65) Prior Publication Data

US 2005/0143796 A1   Jun. 30, 2005

Related U.S. Application Data

(60) Provisional application No. 60/371,314, filed on Apr. 10, 2002.

(51) Int. Cl.
*A61F 7/00* (2006.01)
(52) U.S. Cl. .................. 607/96; 607/104; 607/107
(58) Field of Classification Search .............. 607/96, 607/104, 107, 108; 2/81, 102, 114; 5/423, 5/347
See application file for complete search history.

(56) References Cited

U.S. PATENT DOCUMENTS

| | | | | |
|---|---|---|---|---|
| 2,512,559 A | | 6/1950 | Williams | 5/347 |
| 2,573,414 A | | 10/1951 | Dunn | 128/144 |
| 2,826,758 A | | 3/1958 | Kahn | 2/81 |
| 3,468,299 A | * | 9/1969 | Amato | 126/204 |
| 3,610,323 A | | 10/1971 | Troyer | 165/46 |
| 3,757,366 A | * | 9/1973 | Sacher | 5/423 |

(Continued)

FOREIGN PATENT DOCUMENTS

FR   821150   11/1937

(Continued)

OTHER PUBLICATIONS

Written Opinion of the International Search Authority (EPO) in PCT/US2006/041028, mailed Feb. 20, 2007.
International Search Report and Written Opinion in PCT/US2006/004644, mailed Dec. 18, 2006.

(Continued)

*Primary Examiner*—Roy D Gibson
(74) *Attorney, Agent, or Firm*—Terrance A. Meador; INCAPLAW

(57) ABSTRACT

Apparatus and a system for thermally comforting a patient include pneumatic, convective providing thermal treatment for persons or animals, which is adapted for use in combination with a clinical garment such as a hospital gown, robe, bib, and other equivalents. The pneumatic convective device provides convective warming focused or directly primarily on the thorax or body core. The pneumatic convective device includes at least one inlet for being accessed through a clinical garment, a region in distribution with the inlet for distributing a stream of pressurized, thermally treated air, and a permeable member for emitting pressurized, thermally treated air from the distribution region.

1 Claim, 29 Drawing Sheets

U.S. PATENT DOCUMENTS

| | | | |
|---|---|---|---|
| 3,855,635 A | 12/1974 | Ramirez | 2/114 |
| 3,911,499 A | 10/1975 | Benevento et al. | 2/114 |
| 3,950,789 A | 4/1976 | Konz et al. | 2/93 |
| 4,055,173 A | 10/1977 | Knab | 128/139 |
| 4,146,933 A | 4/1979 | Jenkins et al. | 2/2 |
| 4,369,528 A | 1/1983 | Vest et al. | 2/69 |
| 4,494,248 A | 1/1985 | Holder | 2/69 |
| 4,524,463 A | 6/1985 | Ogden | 2/105 |
| 4,558,468 A | 12/1985 | Landry et al. | 2/51 |
| 4,578,825 A | 4/1986 | Vote | 2/114 |
| 4,587,671 A | 5/1986 | Rodriguez, Jr. et al. | 2/69 |
| 4,651,727 A | 3/1987 | Howorth | 128/201.23 |
| 4,653,120 A | 3/1987 | Leaf | 2/114 |
| 4,696,066 A | 9/1987 | Ball et al. | 2/272 |
| 4,718,124 A * | 1/1988 | Sawicki et al. | 2/114 |
| 4,787,101 A | 11/1988 | Feinberg | 2/105 |
| 4,914,752 A | 4/1990 | Hinson et al. | 2/2 |
| 4,964,282 A | 10/1990 | Wagner | 62/259.3 |
| 5,062,424 A | 11/1991 | Hooker | 128/379 |
| 5,255,390 A | 10/1993 | Gross et al. | 2/2 |
| 5,304,213 A | 4/1994 | Berke et al. | 607/104 |
| 5,360,439 A | 11/1994 | Dickerhoff et al. | 607/104 |
| 5,367,710 A | 11/1994 | Karmin | 2/114 |
| 5,411,541 A | 5/1995 | Bell et al. | 607/104 |
| 5,443,488 A | 8/1995 | Namenye et al. | 607/104 |
| 5,572,742 A | 11/1996 | McFadden | 2/114 |
| 5,575,006 A | 11/1996 | Wolfe | 2/114 |
| 5,611,087 A | 3/1997 | Adkins | 2/114 |
| 5,620,482 A | 4/1997 | Augustine et al. | 607/107 |
| 5,697,963 A | 12/1997 | Augustine | 607/108 |
| 5,733,318 A | 3/1998 | Augustine | 607/104 |
| 5,749,109 A * | 5/1998 | Kappel | 5/423 |
| 5,785,716 A | 7/1998 | Bayron | 607/108 |
| 5,891,187 A | 4/1999 | Winthrop et al. | 607/96 |
| 5,946,722 A * | 9/1999 | Trautmann | 2/83 |
| 5,970,519 A | 10/1999 | Weber | 2/81 |
| 5,974,605 A | 11/1999 | Dickerhoff et al. | 5/421 |
| 6,049,907 A | 4/2000 | Palomo | 2/51 |
| 6,154,883 A | 12/2000 | Spann et al. | 2/69 |
| 6,156,058 A | 12/2000 | Kappel et al. | 607/107 |
| 6,203,567 B1 | 3/2001 | Augustine | 607/104 |
| 6,216,270 B1 | 4/2001 | Moquin et al. | 2/69 |
| 6,235,659 B1 | 5/2001 | McAmish et al. | 442/79 |
| 6,378,136 B2 | 4/2002 | Matsushita | 2/114 |
| 6,484,321 B1 | 11/2002 | Shamam | 2/114 |
| 6,511,501 B1 | 1/2003 | Augustine et al. | 607/96 |
| 6,516,536 B2 * | 2/2003 | Ryden | 34/106 |
| 6,524,332 B1 | 2/2003 | Augustine et al. | 607/107 |
| 6,551,347 B1 | 4/2003 | Elkins | 607/104 |
| 6,571,574 B1 | 6/2003 | Blackstone | 62/420 |
| 6,596,019 B2 | 7/2003 | Turner et al. | 607/108 |
| 6,647,552 B1 | 11/2003 | Hogan | 2/114 |
| 6,694,522 B1 | 2/2004 | Neal | 2/114 |
| 6,792,622 B2 | 9/2004 | Graves | 2/114 |
| 6,799,322 B2 | 9/2004 | Sato | 2/114 |
| 6,820,622 B1 | 11/2004 | Teves et al. | 128/849 |
| 6,851,125 B2 | 2/2005 | Fujikawa et al. | 2/51 |
| 6,876,884 B2 | 4/2005 | Hansen et al. | 607/98 |
| 7,001,416 B2 | 2/2006 | Augustine et al. | 607/104 |
| 7,226,454 B2 | 6/2007 | Albrecht et al. | 607/104 |
| 7,276,076 B2 | 10/2007 | Bieberich | 607/104 |
| 7,364,584 B2 | 4/2008 | Anderson | 607/108 |
| 7,470,280 B2 | 12/2008 | Bieberich | 607/104 |
| 2003/0126668 A1 * | 7/2003 | Scroggins | 2/114 |
| 2005/0015127 A1 | 1/2005 | Bieberich | 607/104 |
| 2005/0143796 A1 | 6/2005 | Augustine et al. | 607/104 |
| 2006/0047332 A1 | 3/2006 | Malmberg et al. | 607/104 |
| 2006/0122671 A1 | 6/2006 | Albrecht et al. | 607/104 |
| 2006/0122672 A1 | 6/2006 | Anderson | 607/104 |
| 2006/0147320 A1 | 7/2006 | Hansen et al. | 417/313 |
| 2006/0184216 A1 | 8/2006 | Van Duren | 607/104 |
| 2006/0184217 A1 | 8/2006 | Van Duren | 607/104 |
| 2006/0184218 A1 | 8/2006 | Bieberich | 607/104 |
| 2006/0259104 A1 | 11/2006 | Panser et al. | 607/104 |
| 2007/0093882 A1 | 4/2007 | Anderson et al. | 607/104 |
| 2007/0093883 A1 | 4/2007 | Anderson et al. | 607/104 |
| 2007/0093884 A1 | 4/2007 | Anderson et al. | 607/104 |
| 2007/0093885 A1 | 4/2007 | Anderson et al. | 607/104 |
| 2007/0239239 A1 | 10/2007 | Albrecht et al. | 607/96 |
| 2008/0027521 A1 | 1/2008 | Bieberich | 607/96 |
| 2008/0027522 A1 | 1/2008 | Bieberich | 607/96 |
| 2008/0125840 A1 | 5/2008 | Anderson | 607/104 |
| 2009/0062891 A1 | 3/2009 | Bieberich | 607/104 |
| 2009/0149931 A9 | 6/2009 | Anderson | 607/104 |
| 2009/0228083 A1 | 9/2009 | Anderson et al. | 607/107 |

FOREIGN PATENT DOCUMENTS

| | | |
|---|---|---|
| GB | 475811 | 11/1937 |
| GB | 1 462 033 | 1/1997 |
| SE | 525 415 | 2/2005 |
| WO | WO 97/14381 | 4/1997 |
| WO | WO 98/48652 | 11/1998 |
| WO | WO 00/62726 | 10/2000 |
| WO | WO 03/086500 A3 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006/086587 A1 | 8/2006 |
| WO | WO 2006086587 A1 | 8/2006 |
| WO | WO 2007/047917 A1 | 4/2007 |
| WO | WO 2008/013603 | 1/2008 |
| WO | WO 2008/091486 | 7/2008 |

OTHER PUBLICATIONS

International Search Report and Written Opinion in PCT/US2005/025355, mailed Dec. 1, 2005.
International Search Report and Written Opinion in PCT/US2005/043968, mailed Apr. 19, 2006.
International Search Report and Written Opinion in PCT/US2005/044214, mailed Apr. 19, 2006.
P.O. Fanger, Thermal Comfort: Analysis and Applications in Environmental Engineering, Danish Technical Press, 1970, pp. 5/67.
C.B. Mahony & J. Odom, Maintaining intraoperative normothermia: A meta-analysis of outcomes with costs. AANA Journal. Apr. 1999.v. 67, No. 2:155-164.
Porta-Chill—The Portable Air-Chiller—Brochure, http://www.portachil.com/, Dec. 3, 2002.
EPO Examination Report mailed Oct. 24, 2006, in EP03719690.4-1526, EP Regional Phase of PCT/US2003/11128 (published as WO/2003/086500).
EPO Examination Report mailed Dec. 17, 2007, in EP03719690.4-1526, EP Regional Phase of PCT/US2003/11128 (published as WO/2003/086500).
International Search Report and Written Opinion in PCT/US2007/013073, mailed Nov. 9, 2007.
EPO Examination Report mailed Sep. 2, 2008, in EP05789978.3, EP Regional Phase of PCT/US2005/025355 (published as WO/2006/020170).
EPO Examination Report mailed Jan. 23, 2009, in EP05853202, EP Regional Phase of PCT/US2005/044214 (published as WO/2006/063027).
International Search Report and Written Opinion in PCT/US2008/000141, mailed Nov. 11, 2008.
EPO Examination Report mailed Sep. 29, 2009, in EP06720577.3.
EPO Examination Report mailed Jun. 22, 2009, in EP05853202.9.
EPO Examination Report mailed May 24, 2009, in EP06826351.6.
EPO Examination Report mailed Sep. 3, 2009 in EP 07795671.2.
EPO Examination Report mailed Apr. 14, 2010 in EP06826351.6.

* cited by examiner

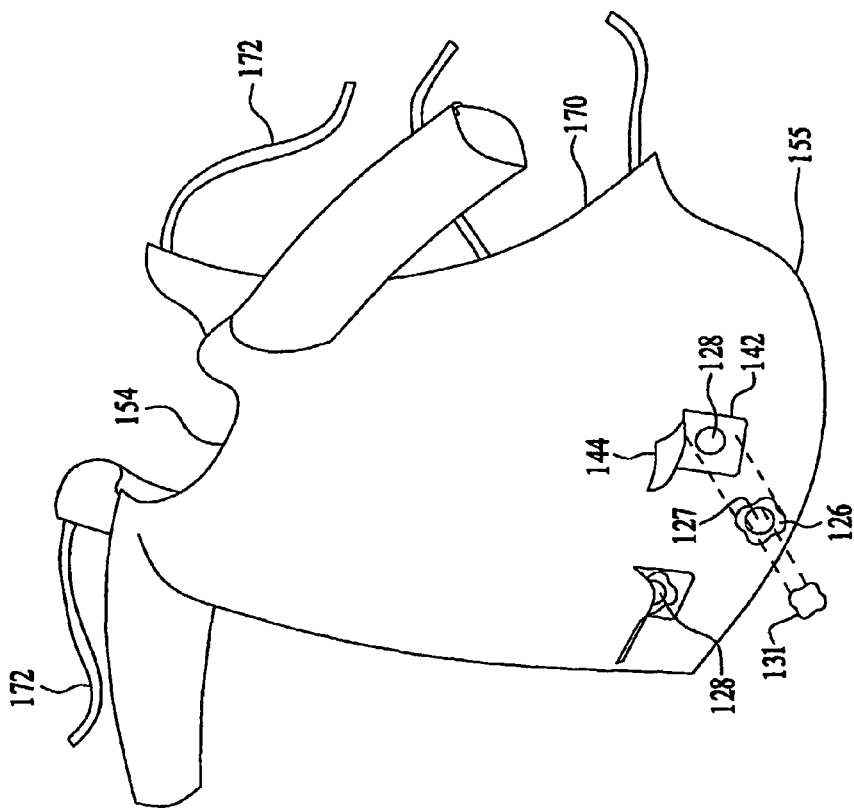
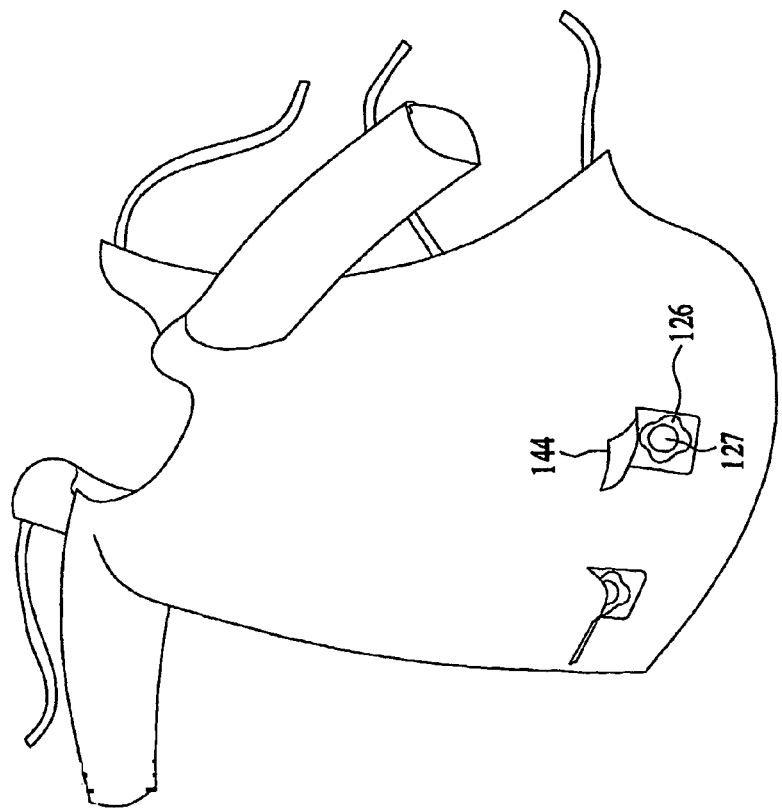

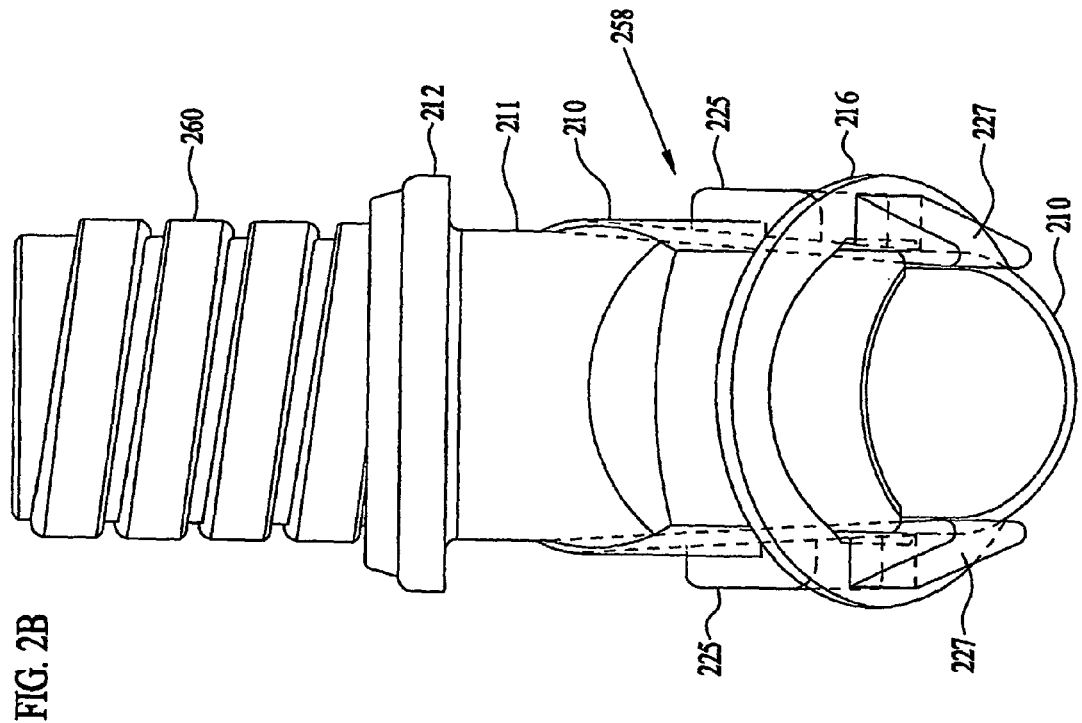
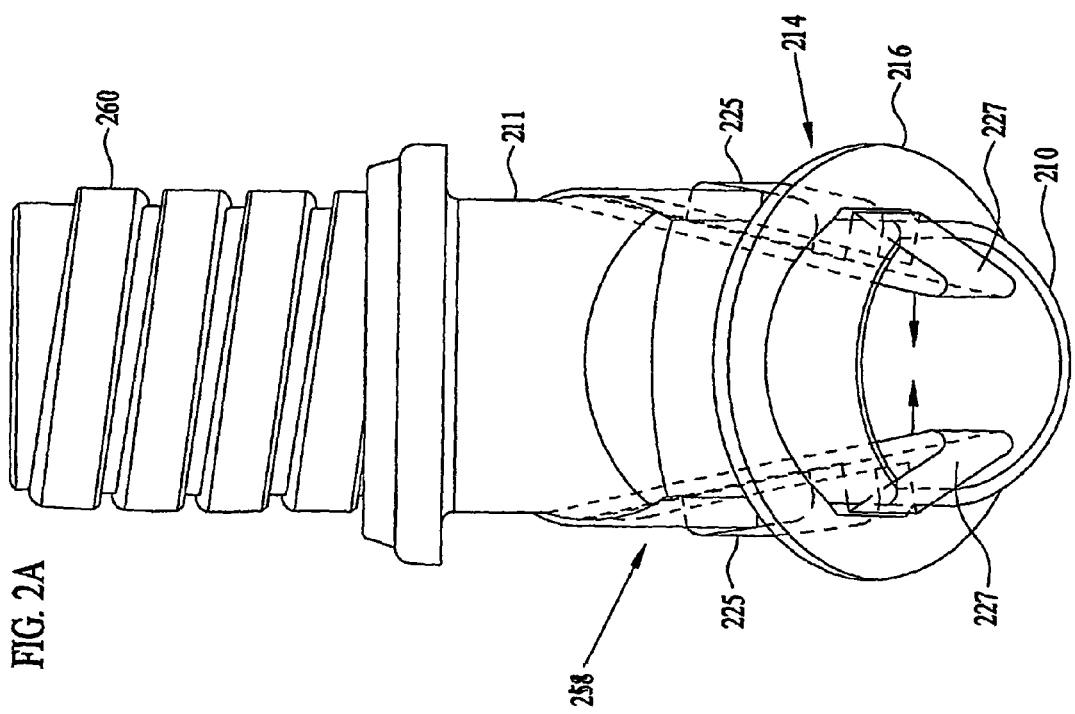

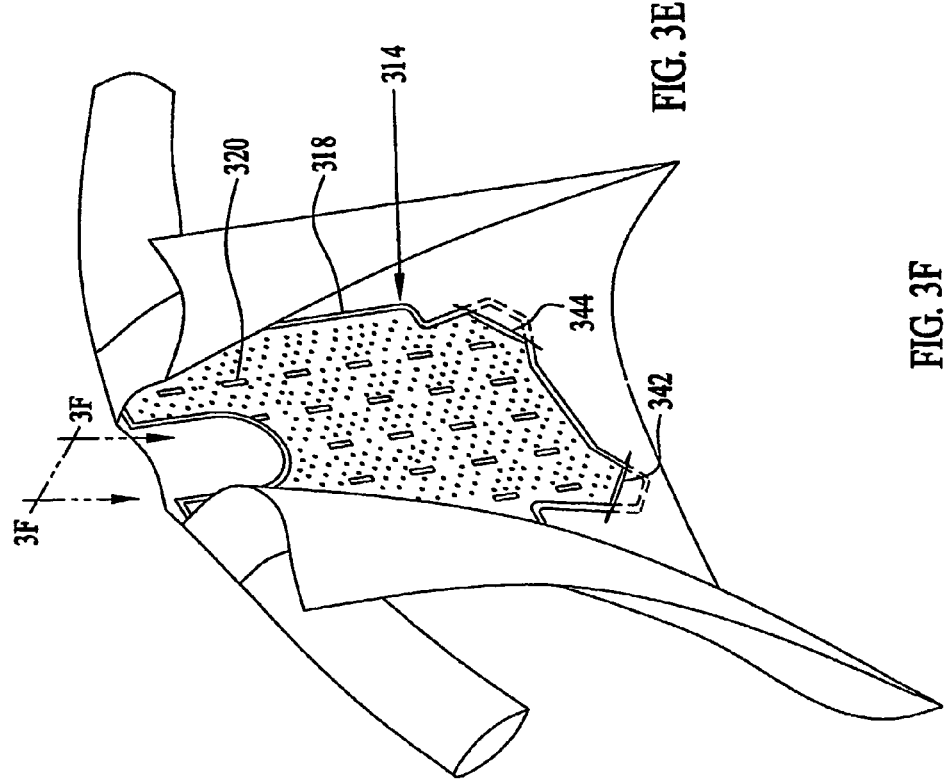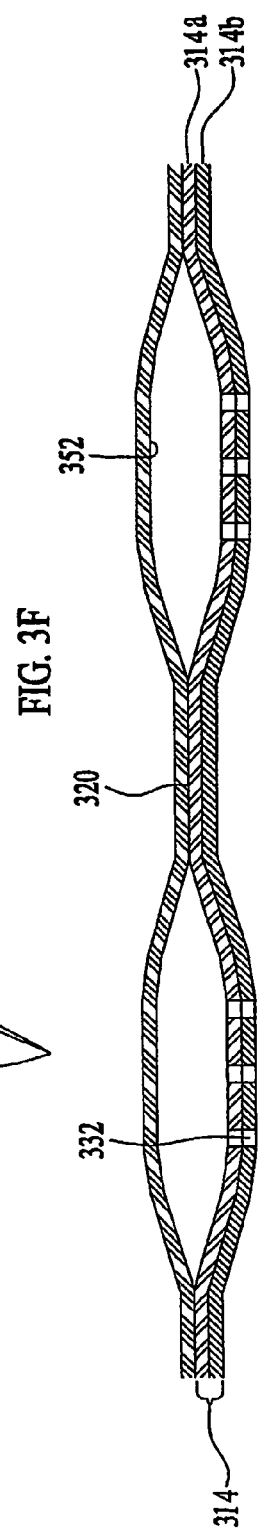

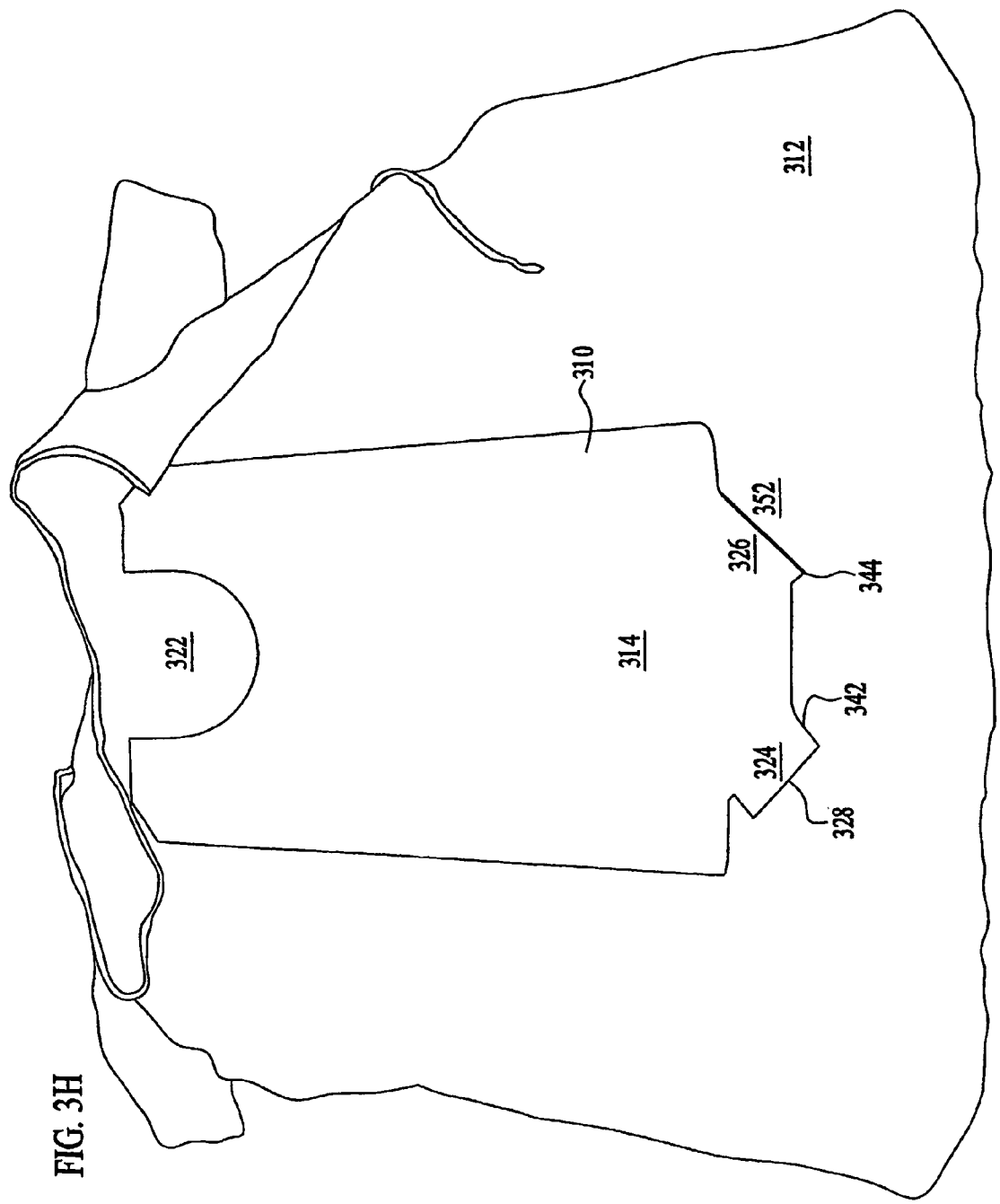

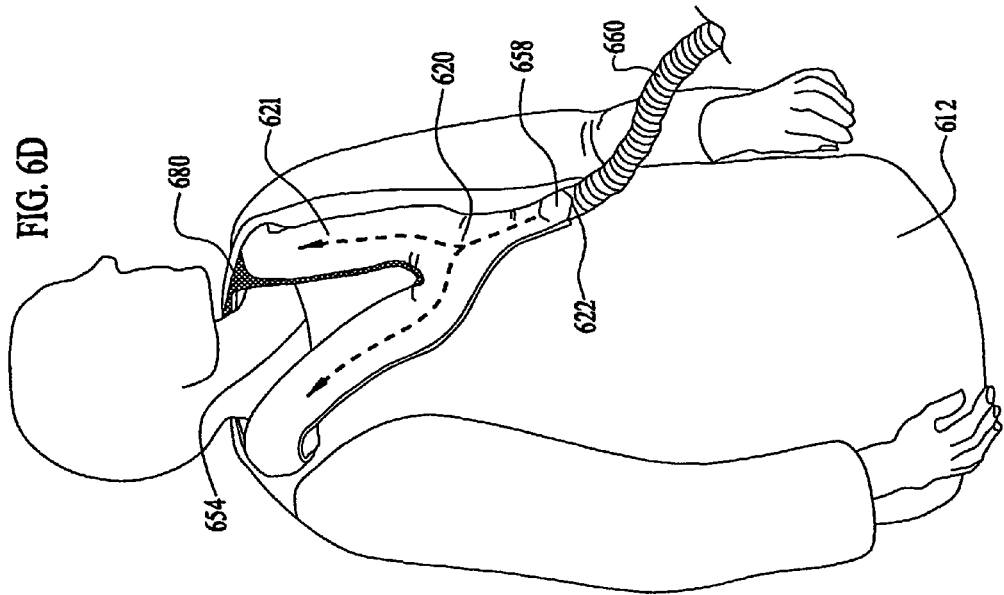
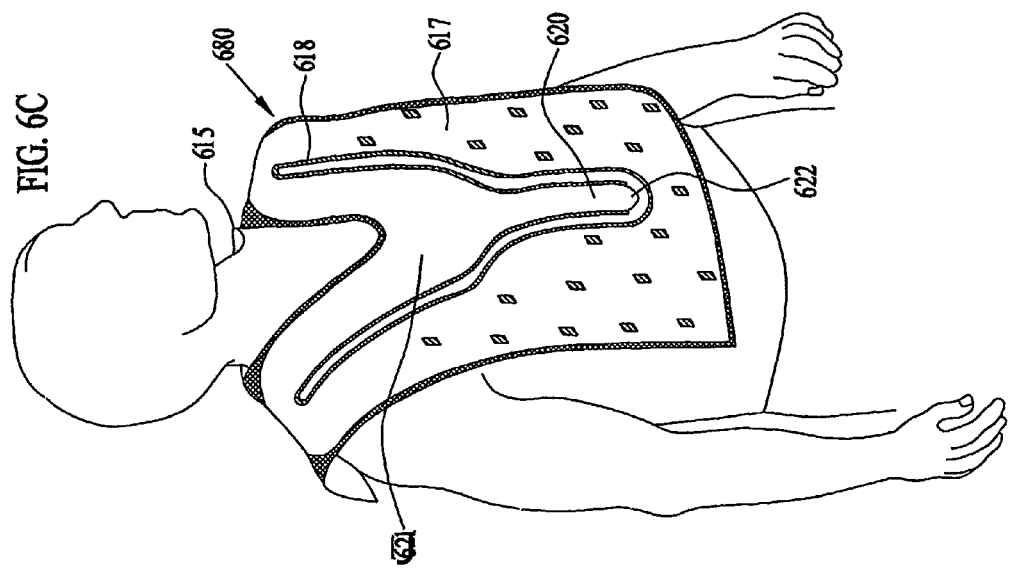

PATIENT COMFORT APPARATUS AND SYSTEM

CROSS REFERENCE TO RELATED APPLICATIONS

This application claims priority under 35 USC § 371 as a United States National Phase application of PCT/US2003/011128, filed Apr. 10, 2003, which claims the benefit of U.S. Provisional Application No. 60/371,314 filed Apr. 10, 2002.

This application contains subject matter related to that of U.S. patent application Ser. No. 10/411,431, for "FORCED AIR WARMING UNIT", now U.S. Pat. No. 6,876,884, and U.S. patent application Ser. No. 10/411,865, for "PATIENT COMFORT APPARATUS AND SYSTEM", now U.S. Pat. No. 7,001,416, both filed concurrently with this application, and to that of U.S. Design Patent Application Ser. No. 29/179,545, filed Apr. 10, 2003, for "FORCED AIR WARMING UNIT", now U.S. Pat. No. D485,338.

This application further contains subject matter related to the subject matter of the following patent applications, all commonly owned herewith:

Patent Cooperation Treaty (PCT) Application No. PCT/US2005/025355, filed Jul. 18, 2005, titled "Perioperative Warming Device", and published on Feb. 23, 2006 under Publication No. WO 2006/020170;

PCT Application No. PCT/US2005/043968, filed Dec. 6, 2005, titled "Warming Device with Varied Permeability", and published on Jun. 15, 2006 under Publication No. WO 2006/062910;

PCT Application No. PCT/US2005/044214, filed Dec. 6, 2005, titled "Warming Device", and published on Jun. 15, 2006 under Publication No. WO 2006/063027;

PCT Application No. PCT/US2006/004644, filed Feb. 9, 2006, titled "Warming Device for Perioperative Use", and published on Aug. 17, 2006 under Publication No. WO2006/086587;

PCT Application No. PCT/US2006/041028, filed Oct. 19, 2006, titled "Multifunction Warming Device for Perioperative Use", and published on Apr. 26, 2007 under Publication No. WO 2007/047917;

PCT Application No. PCT/US2007/013073, filed Jun. 1, 2007, titled "Warming Device", published on Jan. 31, 2008 under Publication No. WO 2008/013603;

PCT Application No. PCT/US2008/000141, filed Jan. 4, 2008, titled "Convective Warming Device With a Drape", published on Jul. 31, 2008 under Publication No. WO 2008/091486;

U.S. patent application No. 10/411,865, filed Apr. 10, 2003, titled "Patient Comfort Apparatus and System", and published on Oct. 16, 2003 under Publication No. US 2003/0195596, now U.S. Pat. No. 7,001,416;

U.S. patent application No. 10/895,672, filed Jul. 21, 2004, titled "Perioperative Warming Device", now abandoned, published on Jan. 20, 2005, under Publication No. US 2005/0015127;

U.S. patent application No. 11/005,883, filed Dec. 7, 2004, titled "Warming Device with Varied Permeability", and published on Jun. 8, 2006 under Publication No. US 2006/0122671, now U.S. Pat. No. 7,226,454;

U.S. patent application No. 11/006,491, filed Dec. 7, 2004, titled "Warming Device", and published on Jun. 8, 2006 under Publication No. US 2006/0122672, now U.S. Pat. No. 7,364,584;

U.S. patent application No. 11/057,396, filed Feb. 11, 2005, titled "Perioperative Warming Device", and published on Aug. 17, 2006 under Publication No. US 2006/0184215, now U.S. Pat. No. 7,276,076;

U.S. patent application No. 11/057,397, filed Feb. 11, 2005, titled "Thermal Blanket for Warming the Limbs", and published on Aug. 17, 2006 under Publication No. US 2006/0184216, now U.S. Pat. No. 7,520,889;

U.S. patent application No. 11/057,403, filed Feb. 11, 2005, titled "Warming Device for Perioperative Use", and published on Aug. 17, 2006 under Publication No. US 2006/0184217;

U.S. patent application No. 11/057,404, filed Feb. 11, 2005, titled "Clinical Garment for Comfort Warming and Prewarming", and published on Aug. 17, 2006 under Publication No. US 2006/0184218, now U.S. Pat. No. 7,470,280;

U.S. patent application No. 11/260,706, filed Oct. 27, 2005, titled "Patient Comfort Apparatus and System", and published on Mar. 9, 2006 under Publication No. US 2005/0052853;

U.S. patent application No. 11/363,136, filed Feb. 27, 2006, titled "Forced Air Warming Unit", and published on Jul. 6, 2006 under Publication No. US 2006/0147320;

U.S. patent application No. 11/492,425, filed Jul. 25, 2006, titled "Warming Device", and published on Nov. 16, 2006 under Publication No. US 2006/0259104;

U.S. patent application No. 11/583,432, filed Oct. 19, 2006, titled "Multifunction Warming Device for Perioperative Use", and published on Apr. 26, 2007 under Publication No. US 2007/0093882;

U.S. patent application No. 11/583,477, filed Oct. 19, 2006, titled "Multifunction Warming Device with Provision for Being Secured", and published on Apr. 26, 2007 under Publication No. US 2007/0093883;

U.S. patent application No. 11/583,480, filed Oct. 19, 2006, titled "Multifunction Warming Device with Provision for Warming Hands", and published on Apr. 26, 2007 under Publication No. US 2007/0093884;

U.S. patent application No. 11/583,481, filed Oct. 19, 2006, titled "Multifunction Warming Device with an Upper Body Convective Apparatus", and published on Apr. 26, 2007 under Publication No. US 2007/0093885;

U.S. patent application No. 11/656,777, filed Jan. 23, 2007, titled "Convective Warming Device With a Drape", and published on Jul. 24, 2008 under Publication No. US 2008/0177361;

U.S. patent application No. 11/704,547, filed Feb. 9, 2007, titled "A Forced Air Warming Unit", and published on Aug. 14, 2008 under Publication No. US 2008/0195184;

U.S. patent application No. 11/801,292, filed May 9, 2007, titled "Warming Device with Varied Permeability", and published on Oct. 11, 2007 under Publication No. US 2007/0239239;

U.S. patent application No. 11/899,872, filed Sep. 7, 2007, titled "Perioperative Warming Method", and published on Jan. 31, 2008 under Publication No. US 2008/0027522;

U.S. patent application No. 11/899,928, filed Sept. 7, 2007, titled "Perioperative Warming Device" and published on Jan. 31, 2008 under Publication No. US 2008/0027521;

U.S. patent application No. 12/011,699, filed Jan. 29, 2008, titled "Warming Device", published on May 29, 2008 under Publication No. US 2008/0125840, and republished on Jun. 11, 2009 under Publication No. US 2009/0149931;

U.S. patent application No. 12/290,713, filed Nov. 3, 2008, titled "Clinical Garment for Comfort Warming and Prewarming", and published on Mar. 5, 2009 under Publication No. US 2009/0062891;

U.S. patent application No. 12/386,243, filed Apr. 15, 2009, titled Warming Device with Provisions for Deploying Elements of an Upper Body Convective Apparatus and for Deploying the Lower Portion of the Warming Device, and published on Sep. 10, 2009 under Publication No. US 2009/0228083, and U.S. patent application No. 12/653,825, filed Dec. 21, 2009, titled "Warming Device Constructions with a Poncho-Type Patient Gown".

BACKGROUND OF THE INVENTION

1. Field of the Invention

The invention is directed to a patient comfort system that includes pneumatic convective devices receivable on a human or animal body which receive a stream of pressurized, thermally conditioned air, distribute the pressurized air within a pneumatic structure, and emit the air through one or more surfaces for convective transfer of heat between the thermally conditioned air and the body. In particular, the invention is directed to the warming of human or animal bodies in a clinical setting by measures that adapt pneumatic convective devices for use with clinical garments, thereby providing thermal treatment to wearers of such garments while permitting movement of the user and enhancing clinical convenience.

2. Description of the Related Art

Pneumatic devices which transfer heat between thermally-conditioned air and a body are known. For example, there are inflatable pneumatic devices that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These inflatable devices are typically characterized as "blankets" or "covers". Arizant Healthcare Inc., the assignee of this application, makes and sells such devices under the BAIR HUGGER® brand. One such device is the Model 522 Upper Body Blanket.

Inflatable pneumatic warming blanket or cover devices are adapted especially for use with supine persons and are typically deployed by being laid directly on a person lying on a bed, a gurney, or a surgery platform, so as to drape over or cover some portion of the person. Because these devices are designed to cover and hang about or over a supine person, they are not easily or readily deployed on persons who are standing, sitting, reclining or moving. In particular, inflatable blankets are not suitable in a clinical setting in which it is desirable to warm a patient, and also necessary that the patient be able to move about and between various postures. In addition, there are a variety of clinical settings in which patient warming is desirable, with each setting requiring its own unique access to patient anatomy that may not be afforded by an inflatable blanket. For example, examination or treatment of a patient in a primary acute care unit (PACU) could call for access to patient lines in the chest area, setting IV's in the arm, application of a stethoscope to the back and/or side, or application of a blood pressure cuff. Further, patient mobility throughout a clinic or a hospital is highly desirable, but would be severely curtailed with use of inflatable blankets. For example, transporting a patient to an x-ray or MRI location in a wheelchair, would be made problematic with an inflatable blanket.

There is also an advantage in not changing established and familiar algorithms of care in which both patients and nurses deal with clinical garments, such as gowns, and nurses know how to deliver care in all circumstances where a patient is wearing a clinical garment. If an inflatable blanket were to be used for warming, a new algorithm would be required to deal with this new element in clinical practice.

One attempt to adapt an inflatable pneumatic blanket for non-supine postures is embodied in U.S. Pat. No. 5,697,963, assigned to Augustine Medical, Inc. and incorporated by reference. In this adaptation, an inflatable pneumatic blanket having a head-section drape is provided with an aperture in the head section drape that is large enough to accommodate the head of a person sitting in a chair. However, this adaptation has a limited use in that a person using it must remain in a sitting or reclining posture in order for the device to drape over the person's body and retain warmed air and heat about the person. Such devices are not designed to accommodate movement or changes in the person's posture or to allow easy access to patient anatomy. These devices are meant to treat hypothermia by driving calories into the patient.

Other inflatable pneumatic warming devices designed for use with supine persons employ tubular structures to at least partially surround a person, and utilize sheets of material extending across the person and the structures to retain warmed air and heat about the person. These devices are even less adaptable than blanket devices for non-supine uses. See, for example, U.S. Pat. Nos. 5,300,101 and 5,674,269, which are incorporated by reference.

A need exists for a pneumatic convective device that achieves the objectives of increased comfort, reduced shivering, and treatment or prevention of hypothermia in a clinical or medical office setting where patients must be able to change postures and enjoy a certain amount of mobility without a significant impact on or change to the treatment algorithm. For example, when visiting a physician for an examination, a patient may be ushered into an examination room, asked to remove clothing in order to permit examination, and given a thin cloth gown to wear while awaiting the physician. In this environment, the patient may be chilled, may shiver, or may be in a condition conducive to hypothermia. Patient anxiety is frequently exacerbated by this cold discomfort. Concomitant with a heightened level of anxiety, patients perceive time as slowing and this anxious waiting period can seem to be prolonged. The cold discomfort can cause a one hour wait to seem like 2 hours to the patient. People tend to vasoconstrict when frightened, and vasoconstriction can lead to reduced peripheral temperature and increased blood pressure, and can make IV access much more difficult. Finally, there is evidence that feeling cold increases the perception of pain. A thin cloth gown provides little in the way of insulation, warmth, and comfort in such circumstances. Therefore, in addition to the patient satisfaction and comfort produced by a bath of thermally-treated air, providing warmth to a cold patient in a medical setting should produce the following unexpected benefits: 1.) reduced blood pressure and easier IV access; 2.) reduced pain sensation; 3.) normalizing of the patient's perception of time slowing; 4.) reduced anxiety and reduced need for medication. These and other objectives are realized when a patient is maintained in a state of thermal comfort. In this regard, "thermal comfort" for a person is defined by P. O. Fanger as "that condition of mind which expresses satisfaction with the thermal environment". Fanger, *Thermal Comfort: Analysis and Applications in Environmental Engineering*, Danish Technical Press, Copenhagen, 1970.

It would be advantageous to provide a course of action, a method, or an instrument by which a patient could be maintained in a state of thermal comfort characterized by a comfortable, healthy temperature while awaiting the physician and even while undergoing examination or treatment. An inflatable blanket or cover could be deployed for this purpose, but would be very impractical because the patient would be required to remain supine or maintain a prone or sitting position. Clinical convenience and utility dictate a more flexible solution in which a pneumatic, convective device serves a warming function in one or more forms that permit movement of the user and of the device itself on the user for examination. It would be particularly advantageous if the solution comported with present modes of treatment that presume the use of clinical garments. For optimal heating, such forms should focus or concentrate the convective effect on the portion of a body being warmed that has the highest concentration of cutaneous thermal receptors. This portion includes the head, neck, chest and abdomen.

Pneumatic devices that thermally condition persons while standing and/or moving are known. One such device, described in U.S. Pat. No. 4,457,295 incorporates a pneumatic, convective means into an article of clothing that is intended for heavy-duty use in an unfriendly environment. The objective of this device is to warm and ventilate by general application of pressurized, heated air through the inside of a closed article of clothing. The pressurized, heated air is provided through a valve system from a source that is convenient to a particular unfriendly environment, such as an exhaust manifold of a motorcycle engine. The article of clothing is fitted to the wearer's body and is closed in order to afford protection against the environment in which the device is deployed. Thus, the device further requires a means for ventilating moisture from within the article of clothing. Its normally closed configuration and complicated pneumatics make this device inconvenient and impractical to use for patient comfort in a clinical environment.

A pneumatic garment, described in U.S. Pat. No. 3,468,299, includes a hooded overcoat intended to be used in unfriendly environments for heating and ventilating a person. This device's structure and operation make it also unsuitable for use in maintaining patient comfort in a clinical environment.

SUMMARY OF THE INVENTION

The invention is based upon the critical realization that garments presently available for use on ambulatory patients can be adapted to provide thermal comfort when combined with a pneumatic convective device. In this regard, lightweight robes or gowns which open at the back or a side, are worn with an open bottom like a skirt or kilt, and are supported primarily at the shoulders and/or neck of the users are referred to as "clinical garments". These clinical garments afford mobility for users; they also provide convenience for clinicians during examination in that they may be easily moved, adjusted, removed, and put back on. Accordingly, the invention provides pneumatic convective thermal treatment of the feeling of being cold by means of pneumatic convective devices adapted for use in combination with clinical garments. The invention also includes the combination of a clinical garment with a pneumatic convective device, as well as a system and method employing such a combination to maintain comfort a patient by warming. The pneumatic convective devices provide effective convective warming that is focused or directed primarily on or to the most thermally sensitive regions of a user. These devices are also simple to manufacture, store, and deploy for use. Finally, because this invention is meant to produce or induce a state of thermal comfort in a patient, without providing hypothermia therapy, airflow exiting the pneumatic convective device of less than 15 CFM (cubic feet per minute) and a temperature of less than 105° F. are preferred.

BRIEF DESCRIPTION OF THE DRAWING

FIGS. 1A-1G illustrate a pneumatic convective device that is combined with a clinical garment according to an embodiment of the invention.

FIGS. 2A-2D illustrate an air hose coupling adapted for use with the pneumatic convective device of FIGS. 1A-1H.

FIGS. 3A-3F illustrate a pneumatic convective device that is combined with a clinical garment according to another embodiment of the invention. FIGS. 3H-3K are photographs showing the pneumatic convective device of FIGS. 3A-3G in use with a hospital gown.

FIGS. 6A-6D illustrate a pneumatic convective device combined with a clinical gown according to yet another embodiment of the invention.

DETAILED DESCRIPTION OF THE PREFERRED EMBODIMENTS

Figure 1A:
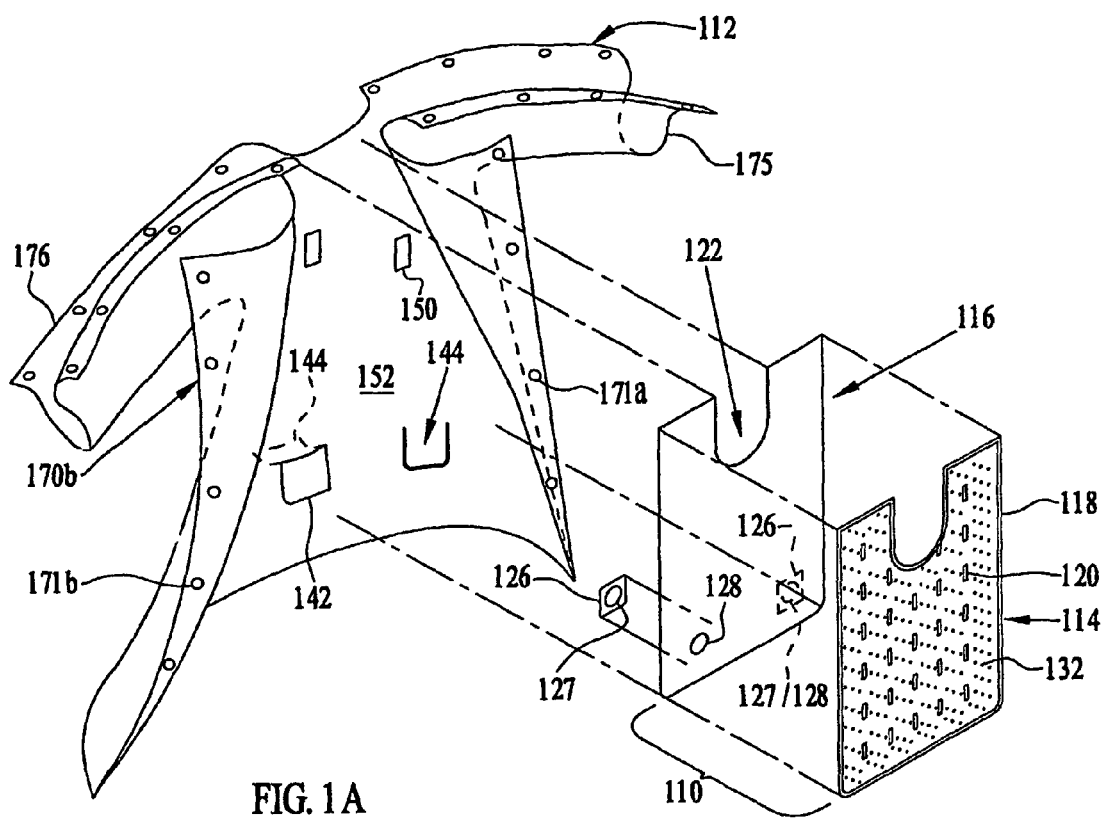

The invention is embodied as a pneumatic convective device receivable on a human or animal body in a clinical setting which receives a stream of pressurized, thermally conditioned air, distributes the pressurized air within a pneumatic structure, and emits the air through one or more surfaces for convective transfer of heat between the thermally conditioned air and the body. The invention is further embodied as a pneumatic convective device combined with a clinical garment to thermally comfort a patient in a clinical setting. Various specific embodiments of the invention are illustrated and discussed according to an example in which a human body is warmed by focusing or concentrating convective warming on the body core in order to permit patient movement and to enhance clinical convenience, although this is not intended to suggest that the invention may not be used for cooling, which, indeed, it may.

Further, use of the term "convective" to denote the transfer of heat to a body refers to the principal mode of heat transfer, it being understood that heat may at the same time be transferred between a device according to this invention and a body by conduction and radiation, although not to the degree of convection.

A pneumatic convective device is adapted for use with a clinical garment that is typically used to temporarily clothe a person in a clinical setting while awaiting and undergoing treatment. Clinical garments include hospital gowns, robes, bibs, and other equivalents. The clinical setting may be a medical, dental, or veterinary office or clinic, a hospital, or any facility or institution that provides treatment to patients.

The pneumatic convective device may be deployed for use with humans, animals, patients, clinicians, practitioners, observers, and so on.

The pneumatic convective device has a pneumatic portion for receiving and distributing at least one stream of pressurized, thermally conditioned air in a structure for being disposed on, adjacent, or next to the core of a body.

The embodiments of the invention illustrated and discussed below are inflatable. That is, their structures, flaccid when not in use, tauten when receiving a stream of pressurized air. The illustrations portray these structures in both inflated and uninflated states, with the understanding that inflation of these embodiments is not necessary to practice of the invention. Indeed, as consideration of the embodiments will make clear, inflatability itself is not necessary to practice of the invention.

In some embodiments, a clinical garment may be specially designed for use with a pneumatic convective device. These specially designed clinical garments would function the same as traditional clinical garments (i.e., temporarily clothe a patient in a clinical setting while awaiting and undergoing treatment), but may include a mounting system for the pneumatic convective device as well as incorporating slits, openings and the like for access to the pneumatic convective device. In other embodiments, the pneumatic convective device is an integral part of the clinical garment.

Figure 1B:
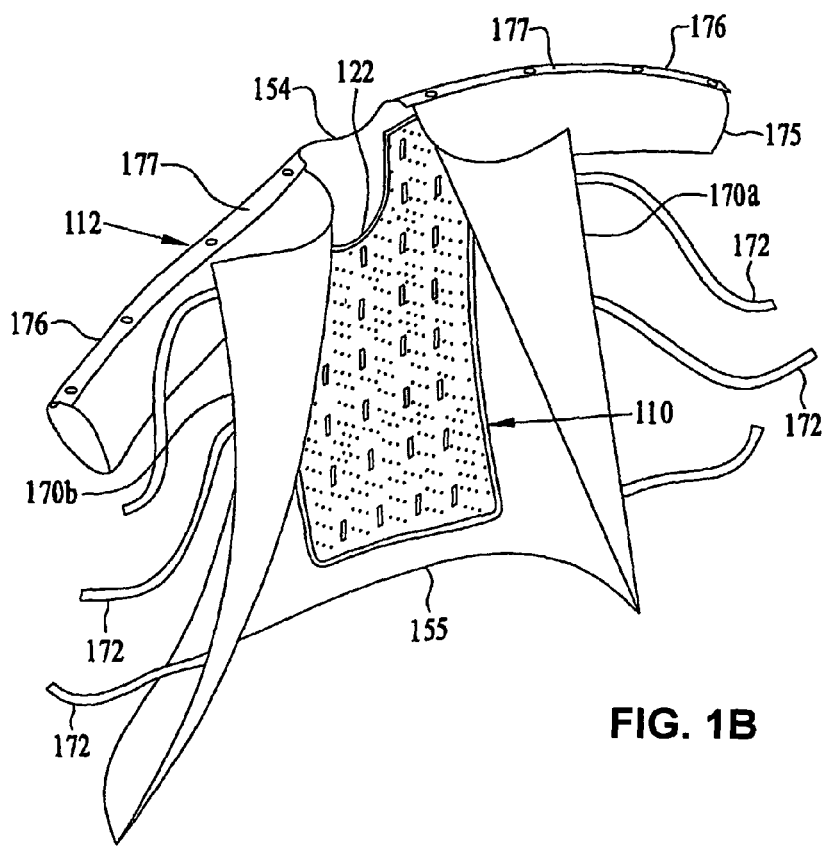
Figure 1C:
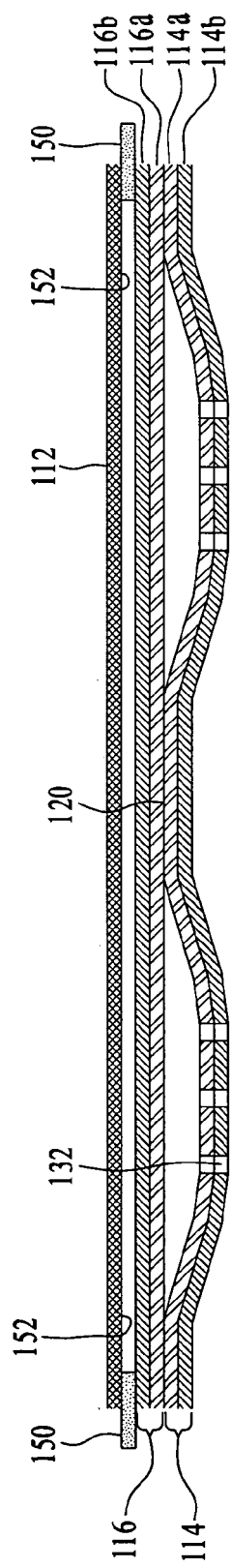

FIGS. 1A-1C illustrate an embodiment of a pneumatic convective device disposed for use with a clinical garment according to this invention. The pneumatic convective device 110 may be attached to or received on a hospital gown 112. The device 110 includes two generally rectangular sheets 114 and 116 of material that are sealed together continuously at their peripheries 118 and intermittently at multiple locations 120 within their peripheries. As shown, the sheets 114 and 116 have the same generally quadrilateral shape, with an optional U-shaped indentation 122 along one edge. At least one opening 128 is provided through the sheet 116 (two openings are shown in the figures), and a quadrilateral hose card 126 with an inlet port 127 is mounted to the sheet 116 over the opening 128, with the inlet port 127 aligned with the hole 128. The at least one opening 128 is provided in communication with the space between the sheets 114 and 116.

The inlet port 127 may receive the end of an air hose from which a stream of pressurized, thermally-treated air flows, through the opening 128, into the space between the sheets 114 and 116. At least one of the sheets 114 and 116 is permeable to air. In this example, only the sheet 114 is air permeable, although this is not intended to so limit the scope of the invention. The permeability of the sheet 114 may be provided by characteristics of the material from which it is formed; alternatively, holes or apertures 132 may be formed in it during the process which joins the sheets 114 and 116. Or, permeability of the sheet 114 may result from the characteristics of its formative material and from formed apertures.

Thus constructed, the sheets 114 and 116 form between themselves a pneumatic structure to receive and distribute pressurized air within itself. At least one permeable member of the device (the sheet 114, for example) cooperates with the pneumatic structure to emit pressurized air from the device. In this regard, one end of an air hose may be received through an inlet port 127. A stream of pressurized, thermally conditioned air introduced through the air hose will fill the space between the sheets 114 and 116 and be distributed throughout the space. The pressurized air is emitted from the pneumatic structure through the air permeable sheet 114 and the motion of the emitted air supports heat transfer with a body adjacent, next to or near the pneumatic structure, facing the permeable sheet 114.

As shown in FIG. 1B, the pneumatic convective device 110 is adapted to be mounted to, received on, supported by or otherwise combined with a clinical garment such as the hospital gown 112. In this embodiment, the gown 112 itself has access openings 142 with flaps 144 through which the inlet ports 127 of the device 110 are accessed. To attach the pneumatic convective device 110 to the gown 112, double-sided adhesive strips 150 may be disposed between the sheet 116 and the inside surface 152 of the grow 112. The adhesion of the sheet 116 with the surface 152 enables the device 110 to be mounted to, received on, supported by or otherwise combined with the gown 112, with U-shaped indentation 122 adjacent the edge 154 of the gown 112 which receives the neck of a user, the sheet 116 facing the inside surface 152, the permeable sheet 114 facing the wearer of the gown 112. In the practice of this invention, the U-shaped indentation 122 is optional, and is not required to practice the invention.

Figure 1E:
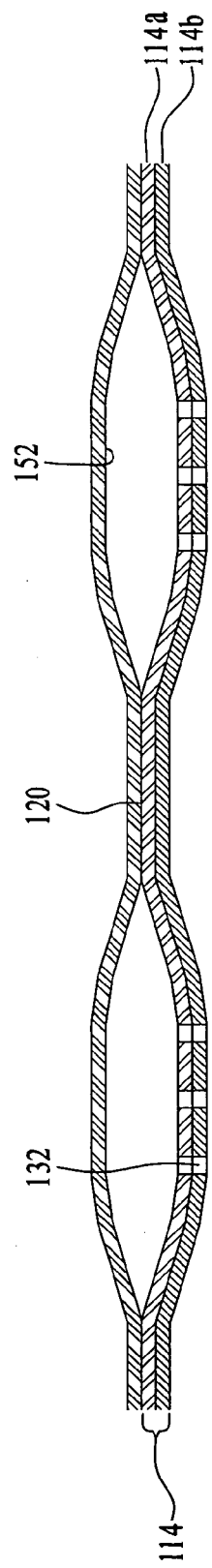
Figure 1H:
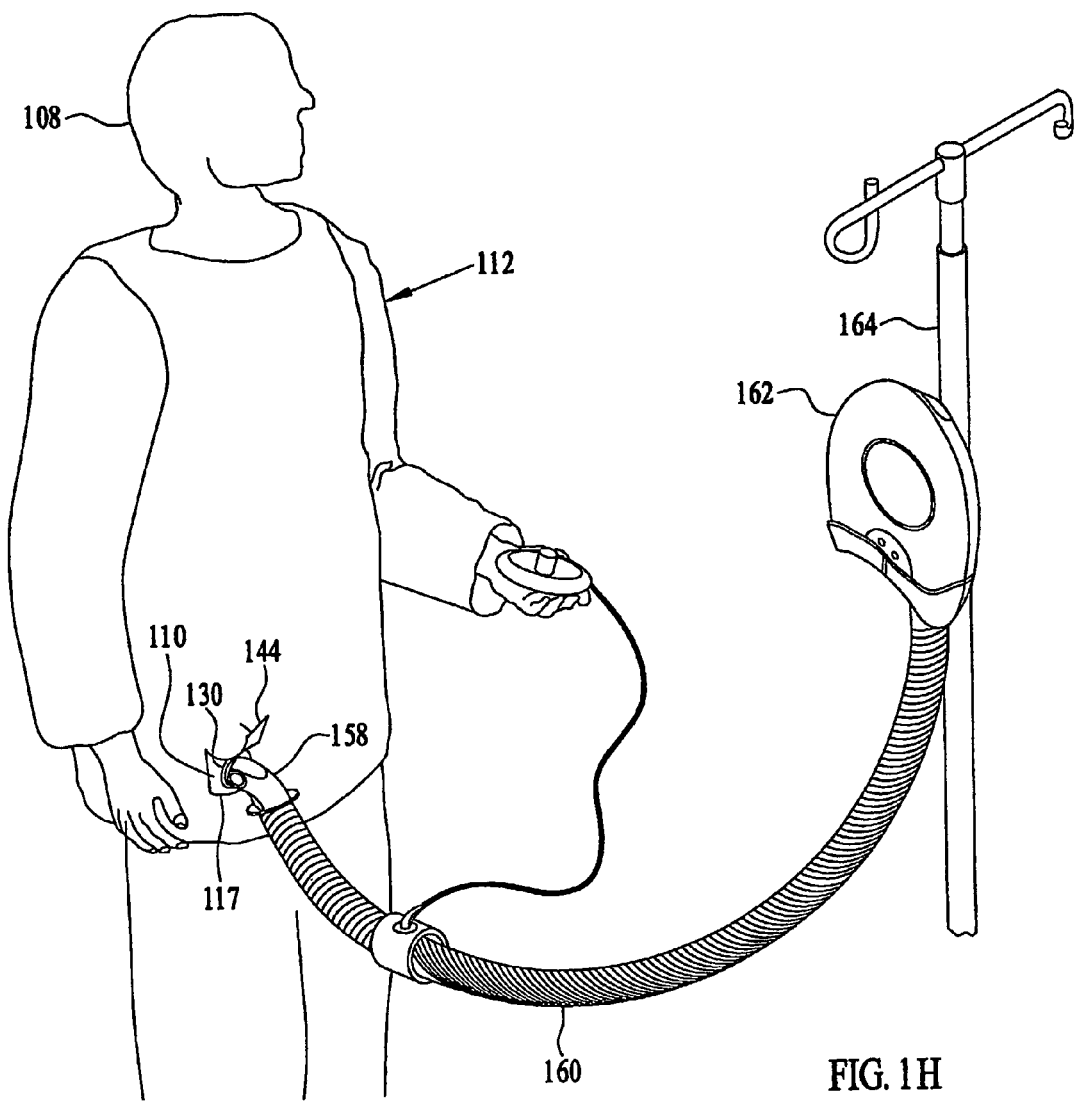
FIG. 1H is a perspective view drawing showing engagement of the combination in a warming system.
Figure 1D:
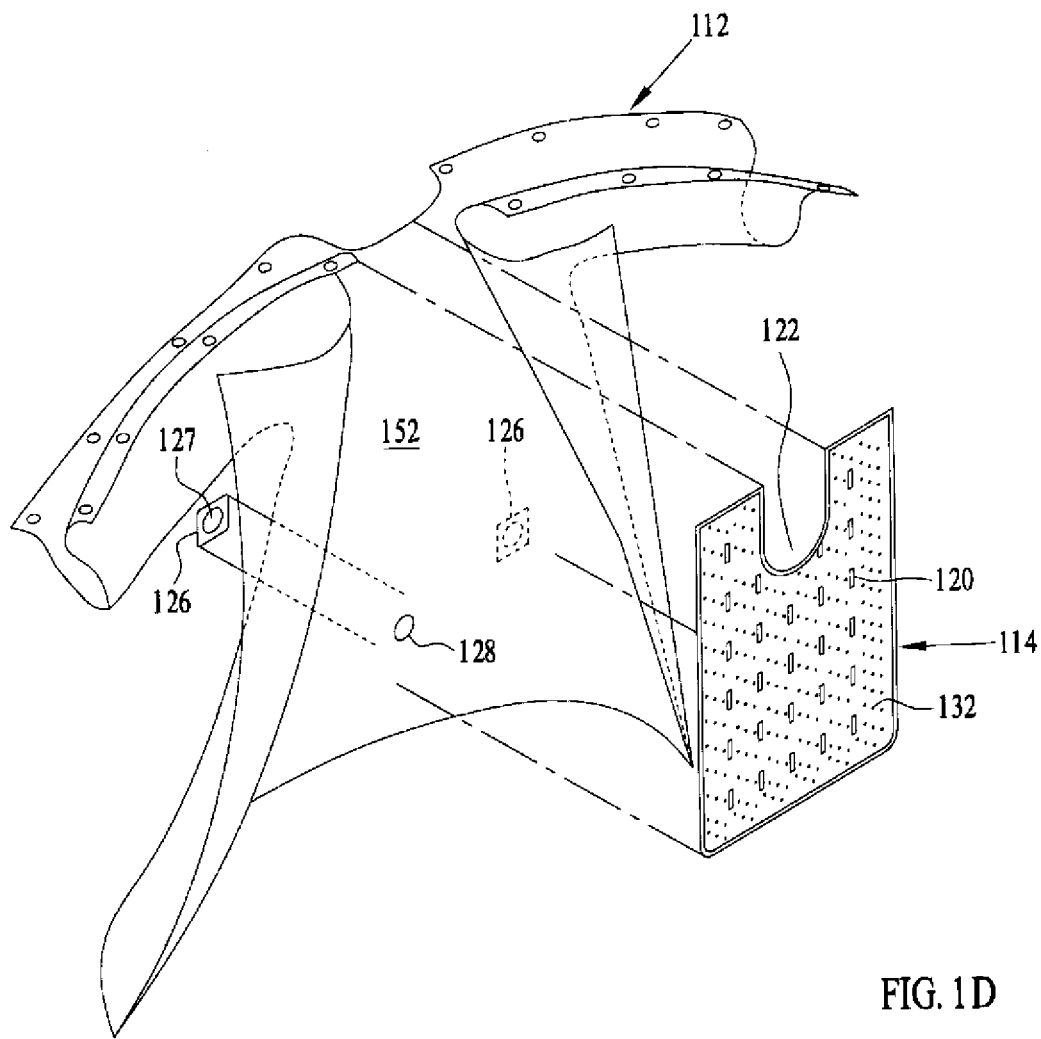

A variant of the pneumatic convective device of FIGS. 1A-1C is illustrated in FIGS. 1D-1E. In this variant, a portion of the inner gown surface 152 is incorporated into the structure of the device 110, serving in the role of the sheet 116 in FIGS. 1A-1C. Otherwise, the structure and operation of the device 110 are as already described.

Alternatively, the device shown in FIGS. 1D-1E may be constructed with an impermeable sheet on the outside of the gown 112, wherein the portion of the gown 112 that includes the inner gown surface 152 would serve as the permeable sheet.

Refer to FIGS. 1C and 1E for an understanding of how each of the embodiments shown in FIGS. 1A and 1D may be constructed. The sheets 114 and 116 may have an identical laminate structure in which a layer (114a, 116a) of extruded synthetic material is lined with a layer (114b, 1161b) of non-woven material. If a laminate structure is selected, holes or apertures 132 are formed through both layers 114a, 114b of the sheet 114. In FIG. 1C, the sheets 114 and 116 are oriented to have the extruded layers (114a and 116a) facing, and the seals 118, 120 are formed by a gluing process or by a heating or ultrasonic process acting through one of the layers of non-woven material. In FIG. 1E, the sheet 114 may be a laminate structure as described above. The gown 112 is a woven cloth, such as cotton, or a non-woven such as spunbond-meltblown-spunbond material (SMS), and the seals between the portion of its inside surface 152 and the extruded layer of the laminate sheet may be formed by a gluing, a heating, or an ultrasonic process. Examples of non-woven material include any one or more of polyester, cotton, rayon, polypropylene, and wood pulp. Examples of extruded synthetic material include polypropylene, polyesters, and polyurethanes. Examples of attachment materials and mechanisms by which the device 110 as presented in FIG. 1A can be attached to the gown 112 include two-sided adhesive, hook and loop, sewing, snaps, heat, ultrasonic, rivets, and any and all equivalents thereof.

FIGS. 1F-1G show the front of the gown 112. The inlet ports 127 are accessible from the front of the gown 112. There may be one or more inlet ports 127 providing access through openings 128. In these cases, it may be desirable to plug an inlet port 127. An inlet port plug 131 may be used to close the inlet ports 127 that are not in use with the air hose. Many types of plug may be used to close the inlet ports 127, such as those described in U.S. Pat. No. 5,997,572, which is incorporated herein by this reference.

FIG. 1H illustrates a patient 108 in the standing position wearing the gown 112, which includes the pneumatic convective device 110, as described above. The patient may be in a doctor's office in an out-patient facility, or other suitable location. The gown 112 is shown with connecting lines that illustrate how it would be attached to the patient. An end 158 of an air hose 160 is connected to the pneumatic convective device 110 may received with the hose card 130 to provide a stream of pressurized, thermally treated air directed into the device 110 through inlet port 127. For the embodiment shown in FIGS. 1A-1C, the flap 144 is lifted, exposing the inlet port 127 and the hose card 130, through an access opening 142. For the embodiment shown in FIGS. 1D-1E, access to the hose card 130 is on the front of the gown 112 (there is no access opening). The other end of the air hose 160 is connected to a warming unit 162 that can provide a stream of pressurized, thermally controlled air to the device, like the one described in co-pending, concurrently filed patent application "FORCED AIR WRMING UNIT" which is incorporated herein by this reference. The temperature at the hose-end 158, prior to the air entering the pneumatic convective device 110, may range from ambient to 42° C. The average air temperature delivered to the patient may be less than this, depending on the gown design. The airflow at the hose-end 158, prior to the air entering the pneumatic connective device 110, may be between 5-15 CFM. The pressure inside the pneumatic convective device 110 may range of 0.25 to 0.75 inches $H_2O$. The warming unit 162 may be mounted on an IV pole 164, as illustrated.

When the stream of pressurized, thermally treated air is provided to the device 110, the device 110 tautens and air is emitted through the sheet 114, treating the person 108 with thermally controlled air. As can be appreciated with reference to FIG. 1H, with the gown 112 worn by a person 108, the device 110 is disposed so that the permeable sheet 114 faces the person 108 primarily in the region between the person's neck and thighs. Thus when pressurized, thermally treated air is provided to the device 110, it is distributed within the device, and emitted through the sheet 114, focusing or concentrating the emitted air primarily on the person's upper thorax. Convection will then cause heat transfer between the emitted, thermally treated air and the person's body core or diminish heat loss from the person's body to the environment.

The clinical garment described in the above and in below-described embodiments may be a standard gown, a modified gown or a special purpose gown. The gowns may have rear openings, front openings or other openings suitable openings, such as a head opening in a poncho type gown. One type of gown shown in the figures has a rear opening. Referring now to FIGS. 1A-1B, the gown 112 has a slit 170 that extends from the neck portion 154 to a hemline 155. To attach the gown 112 to a patient, there is a fastening means provided to provide for ease in securing the gown to the patient as well as allowing for ease in adjusting the size of the gown to accommodated various different size wearers. FIG. 1A shows one method using hook and eye buttons 171*a*, 171*b* positioned along opposing sides of the slit 170*a*, 170*b* that can be brought together and fastened to hold the gown to the patient. Another method attachment shown is a plurality of strings 172 positioned along opposing sides of the slit 170*a*, 170*b* that can be tied together for hold the gown to the patient. Other methods of attachments include hook and eye elements, double-sided adhesive, snaps, rivets, and any and all equivalents thereof.

In some embodiments, the clinical garment may include sleeves that are sized and positioned for receiving a patients arms. Two examples of suitable sleeves are shown in the figures. In FIGS. 1A-1B, the sleeve portions 175 have slits 176 that run the entire length on the shoulder or top 177. This allows access to the upper body of the patient and allows for opening and closing of the slits 176 in an adjustable fashion using Velcro buttons, snaps, repositionable adhesive, hook and eye elements, double-sided adhesive, hook and loop, rivets, and any and all equivalents thereof. The design shown in FIG. 1A also facilitates the manufacturing of the gown 112 in one piece. Another embodiment shown in FIGS. 3A-3B has sleeves 374 are attached to the main or body portion of the gown 312 and are not openable.

Figure 2C:
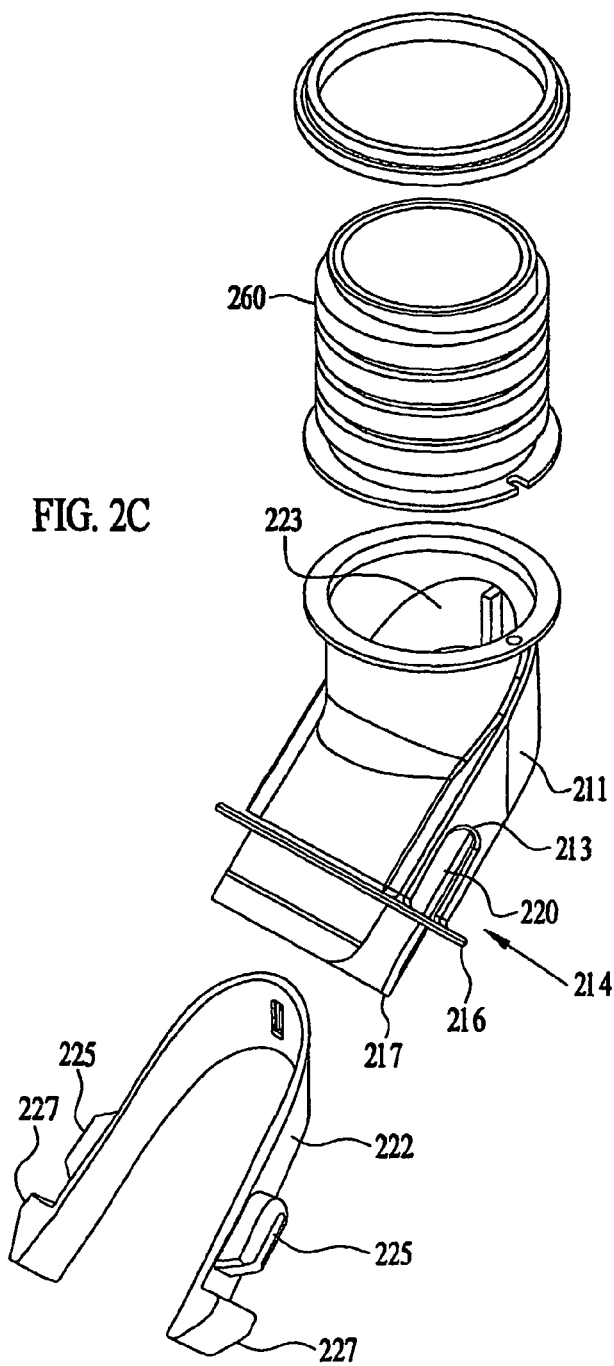
Figure 2D:
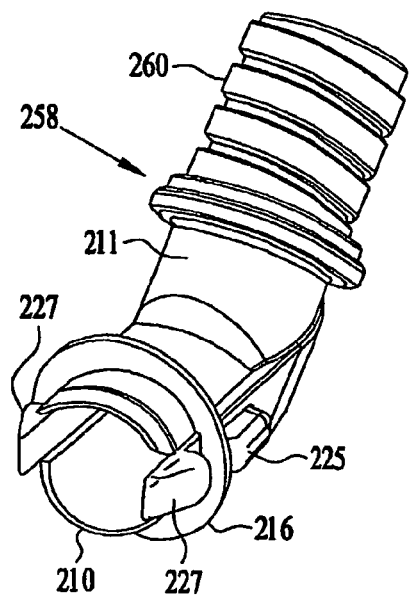

In FIGS. 2A-2D, an air hose 260 has an end 258, which is in the form of a nozzle 210 attached to the air hose 260 at an annular junction 212. The nozzle 210 may transition from a tubular rear section 211 through an angle less than 90° to a tubular forward section 214. It is desirable that the nozzle 210 be provided with a mechanism to releasably couple it with a hose card of one of the pneumatic convective devices of FIGS. 1A-1F. An example of such a mechanism is shown in these figures. Opposing slots 220 are cut longitudinally along the forward section 214 of the nozzle, extending to its end 217. An annular flange 216 is formed circumferentially around the forward section 214 seated over the slots 220, back from the end 217. A flexible U-shaped latch 222 comprising opposing tongs is mounted to the inside of the nozzle 210, extending from the end 217 where the tongs are received in the slots 220, to the end of the rear section 213 in which a groove 223 is cut to receive and seat the spring end of the U-shaped latch 222. Finger pieces 225 mounted on the outsides of the tongs are received in the slots 220, behind the annular flange 216. The tongs have wedge-shaped pieces 227 mounted to their ends, forward of the annular flange 216. As best seen in FIG. 2A, the tongs of the latch 222 flex together toward the interior of the nozzle, away from the slots 220 in response to pressure applied to the finger pieces 225. According to the illustration in FIG. 2B, when the pressure is released, the tongs spring back to the annular flange 216. With reference to FIGS. 1H, 2A, and 2B, in operation, the nozzle 210, on the end of the air hose 260 is brought to an inlet port 127, the tongs are flexed together as in FIG. 2A and the end of the forward section 214 is inserted into the inlet port 127 far enough for the annular flange 216 to abut the hose card 126. The flexing pressure on the tongs is released and the tongs spring back against the annular flange 216. The hose card is held between the wedge-shaped pieces 227 and the annular flange 216, thereby maintaining the air hose 260 engaged or coupled to the pneumatic convective device served by the input port 127. The nozzle 210 can be disengaged or decoupled from the device by squeezing the tongs of the latch 222 together and removing the forward section 214 of the nozzle from the inlet port 127.

Preferably, the diameter of the inlet port is larger than that of the nozzle to allow for easy entry of the nozzle. As the latch is engaged, the nozzle is secured against the inlet port perimeter and abuts the annular flange, thus securing the fit to reduce or eliminate air leakage where the inlet port and the nozzle are joined. The nozzle may also be configured to swivel to accommodate the diverse range of motion the devices will experience in various settings.

Figure 3A:
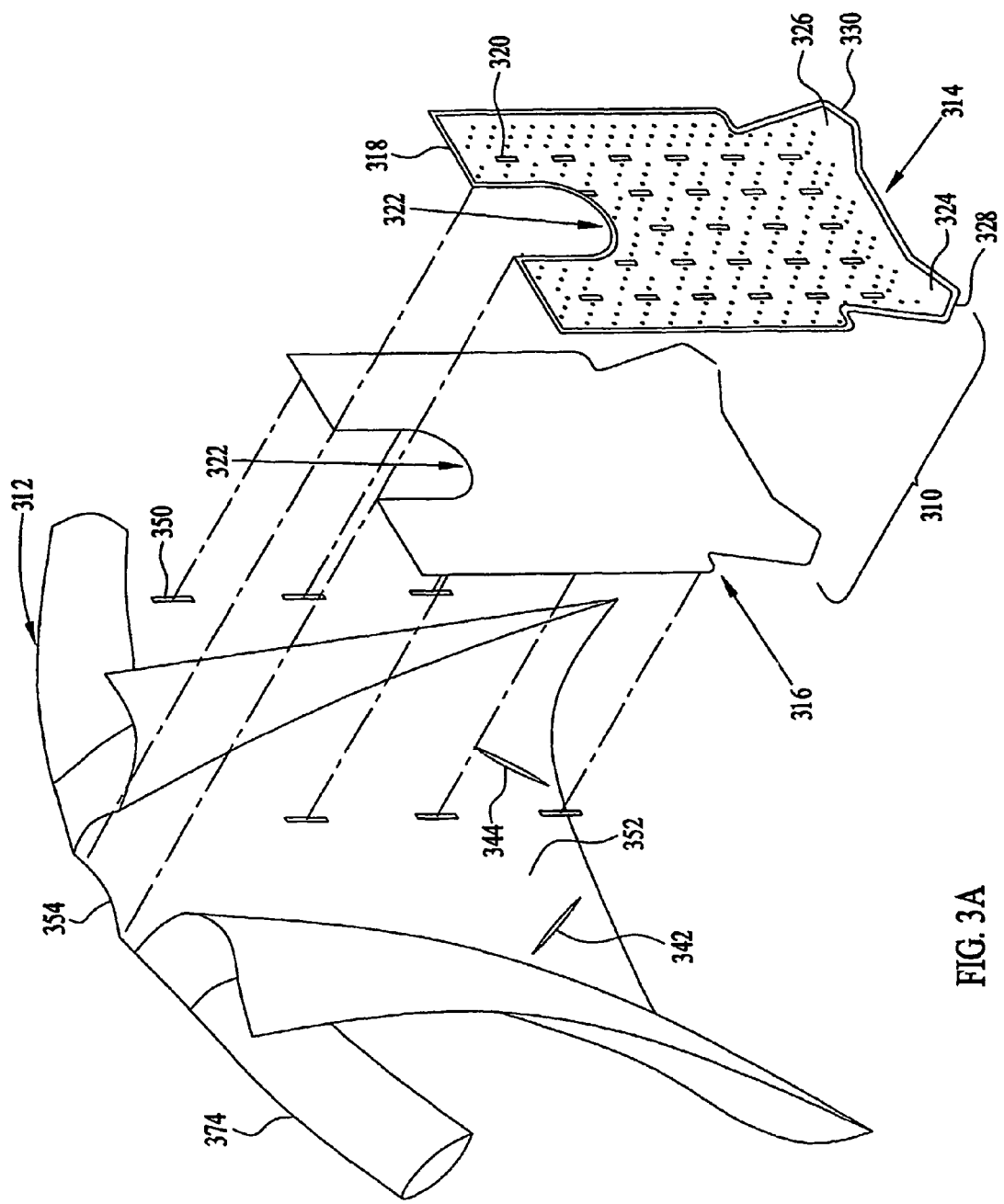
Figure 3B:
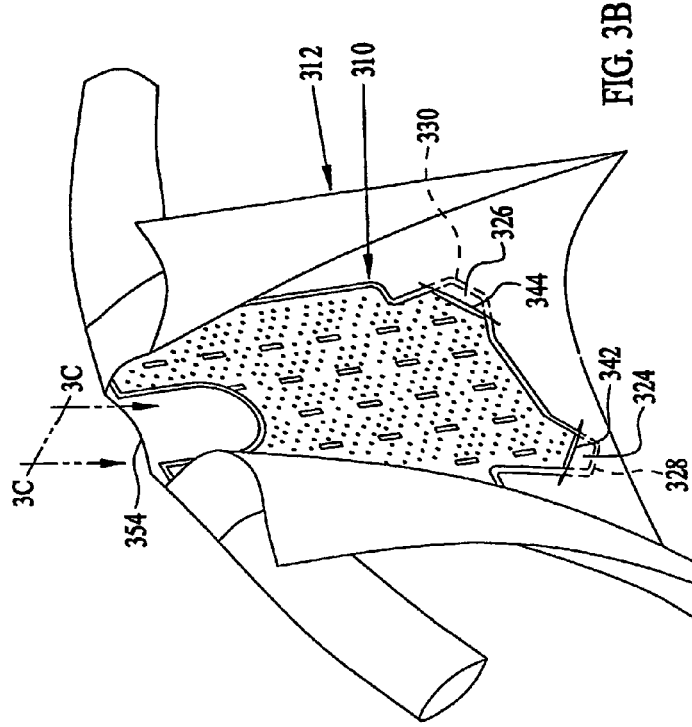
Figure 3C:
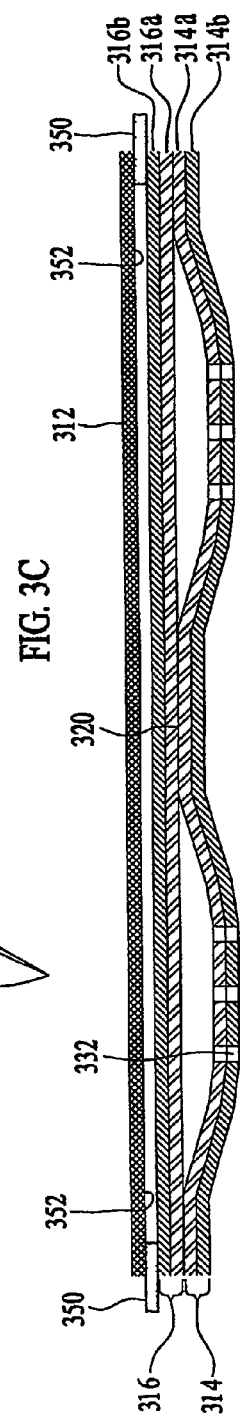

Another embodiment of an exemplary pneumatic convective device is illustrated in FIGS. 3A-3C. Here, a pneumatic convective device 310 according to an embodiment of the invention is attachable to a clinical garment or hospital gown 312. The device 310 includes two sheets 314 and 316 of material that are sealed together continuously at their peripheries 318 and intermittently at multiple locations 320 within their peripheries. As shown, the sheets 314 and 316 have the same generally quadrilateral shape, with an optional U-shaped indentation 322 along one edge. At the corners of an opposing edge, the sheets 314 and 316 have projections 324 and 326. The seal at the ends 328 and 330 of the projections 324 and 326 may be broken, so that at least one opening is provided in communication with the space between the sheets 314 and 316. The opening may receive the end of an air hose from which a stream of pressurized, thermally-treated air flows, through the opening, into the space between the sheets 314 and 316. At least one of the sheets 314 and 316 is permeable to air. In this example, only the sheet 314 is air permeable, although this is not intended to so limit the scope of the invention. The permeability of the sheet 314 may be provided by characteristics of the material from which it is formed; alternatively, holes or apertures 332 may be formed in it during the process which joins the sheets 314 and 316. Or, permeability of the sheet 314 may result from the characteristics of its formative material and from formed apertures.

Thus constructed, the sheets 314 and 316 form between themselves a pneumatic structure that may receive and distribute pressurized air within itself. At least one permeable member of the device (the sheet 314, for example) cooperates with the pneumatic structure to emit pressurized air from the device. In this regard, one end of an air hose may be received through an opening in either of the ends 328 and 330. A stream of pressurized, thermally conditioned air introduced through the air hose will fill the space between the sheets 314 and 316 and be distributed throughout the space. The pressurized air is emitted from the pneumatic structure through the air permeable sheet 314 and the motion of the emitted air supports heat transfer with a body adjacent, next to or near the pneumatic structure, facing the permeable sheet 314.

Figure 3D:
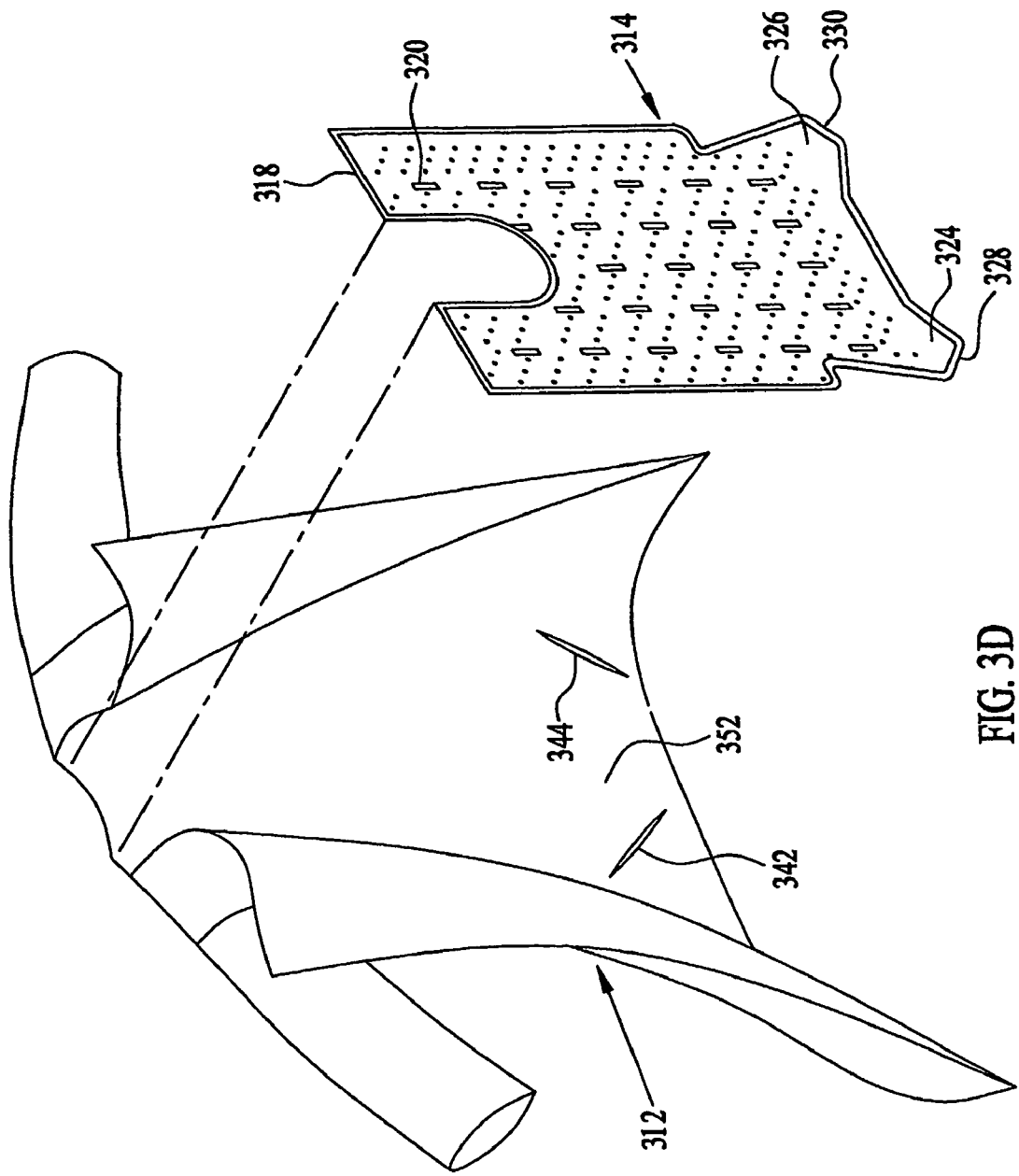
Figure 3G:
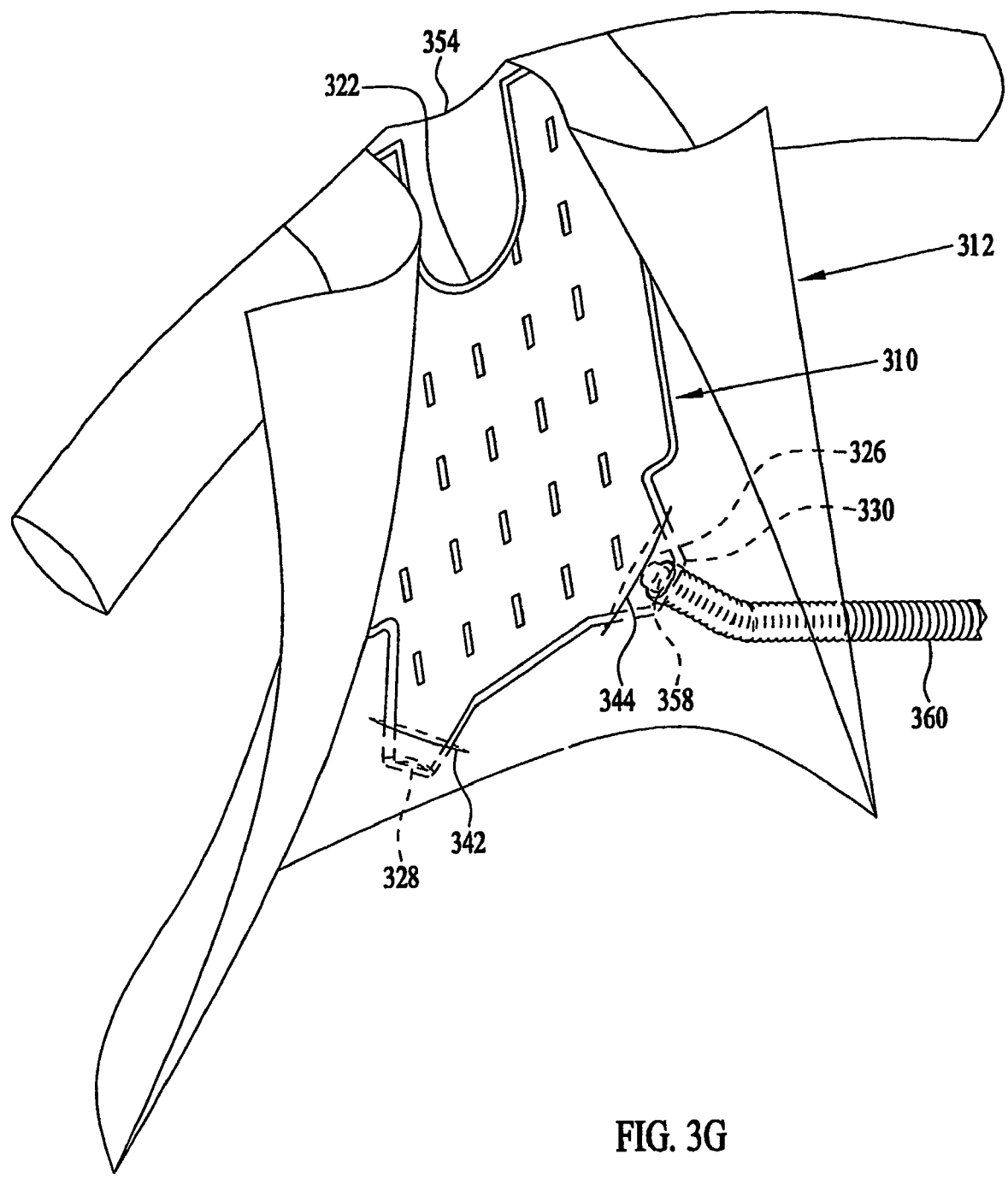
FIG. 3G is a perspective view drawing showing engagement of the pneumatic convective device with an air hose.
Figure 31:
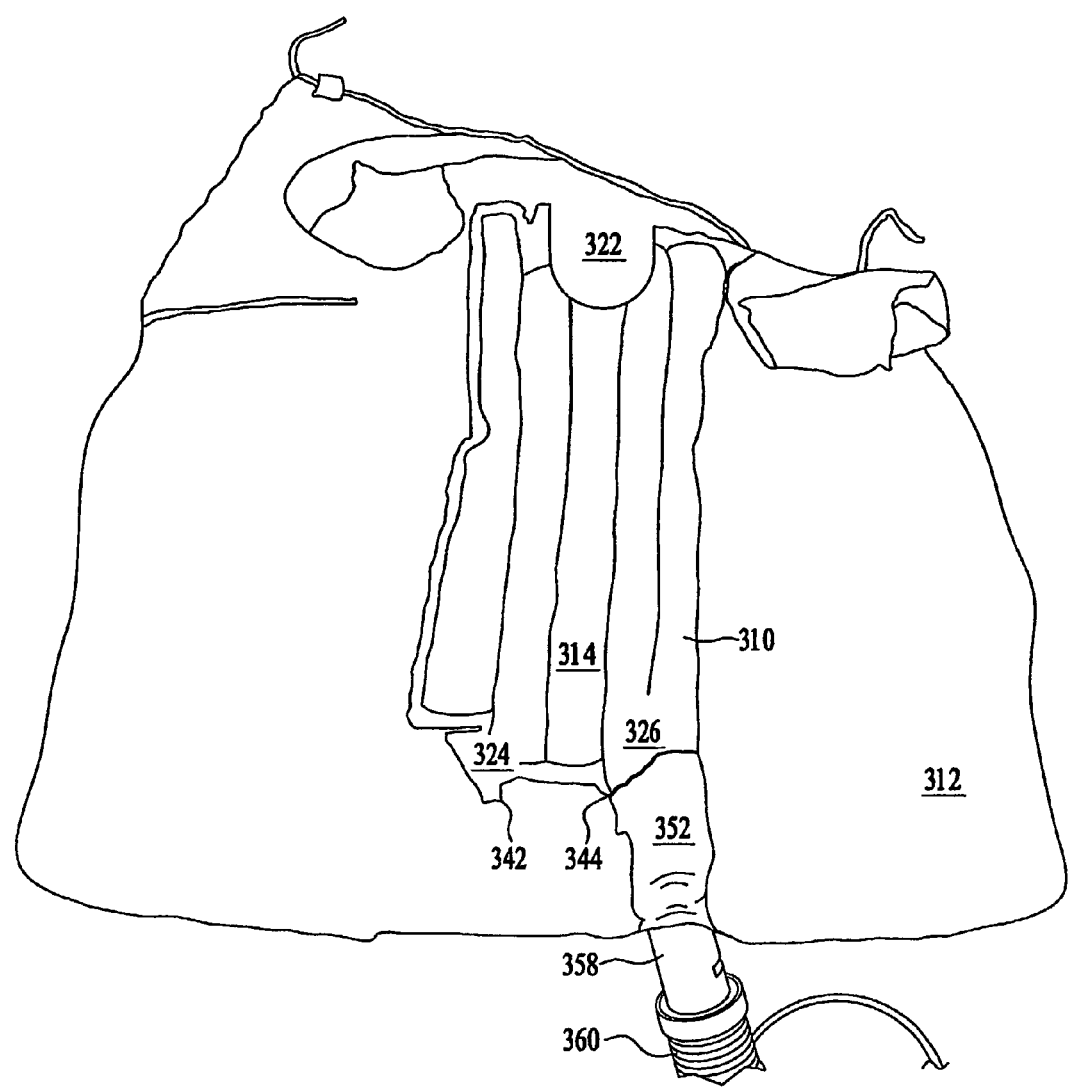
Figure 3J:
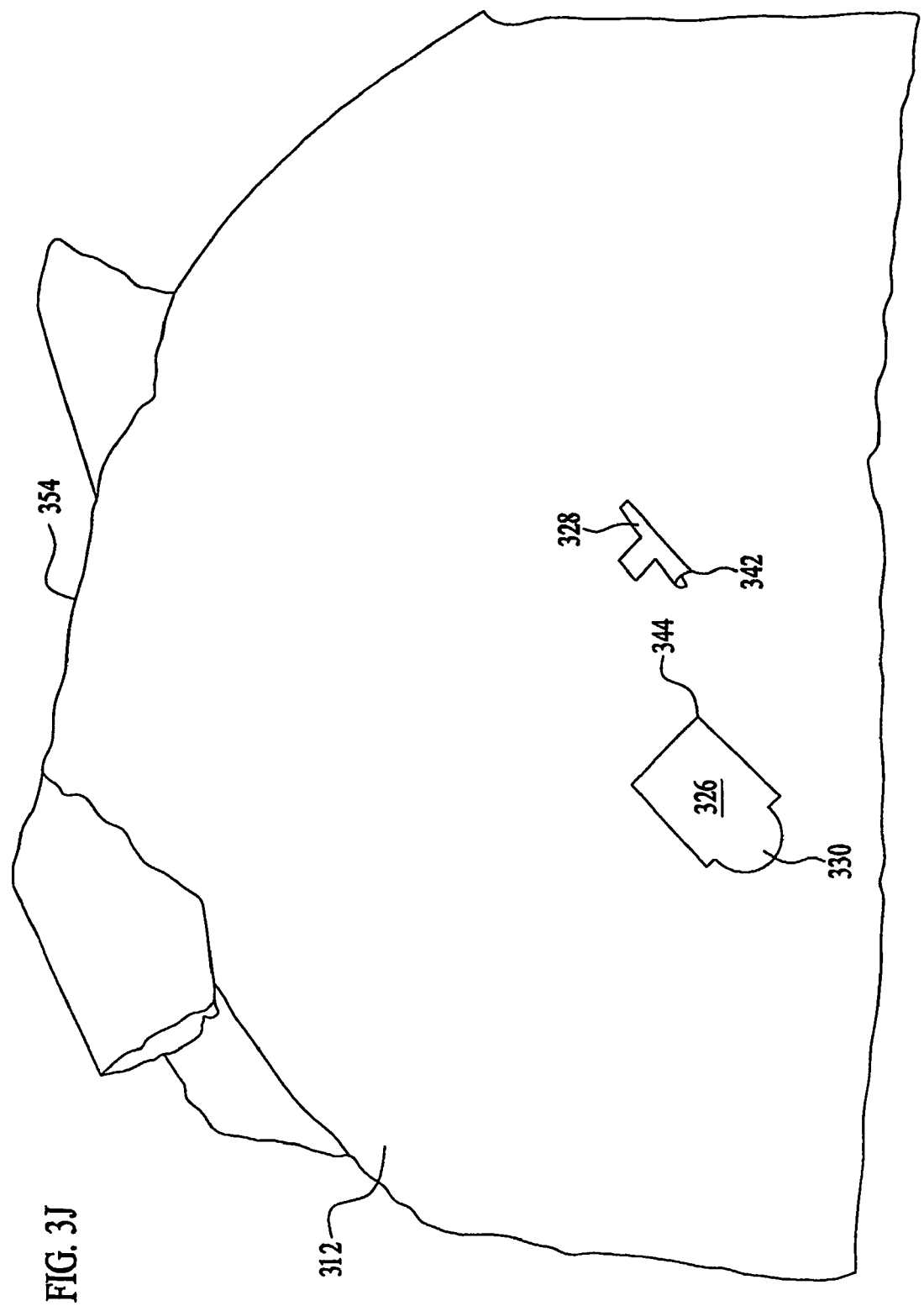

As shown in FIGS. 3B, 3H, and 3J, the pneumatic convective device 310 is adapted to be mounted to, received on, supported by or otherwise combined with the hospital gown 312. In this embodiment, the gown 312 itself has slits 342 and 344 through which the ends 328 and 330 of the device 310 are received. In addition, double-sided adhesive strips 350 are disposed between the sheet 316 and the inside surface 352 of the gown 312. The interconnection of the ends 324, 326 with the slits 342, 344 and the adhesion of the sheet 316 with the surface 352 enable the device 310 to be mounted to, received on, supported by or otherwise combined with the gown 312, with the U-shaped indentation 322 adjacent the edge 354 of the gown 312 which receives the neck of a user, the sheet 316 facing the inside surface 352, the permeable sheet 314 facing the wearer of the gown 312, and the ends 324, 326 extending through the outside surface of the gown 312. (Note that the U-shaped indentation 322 is optional, and is not required to practice the invention.)

Figure 3K:
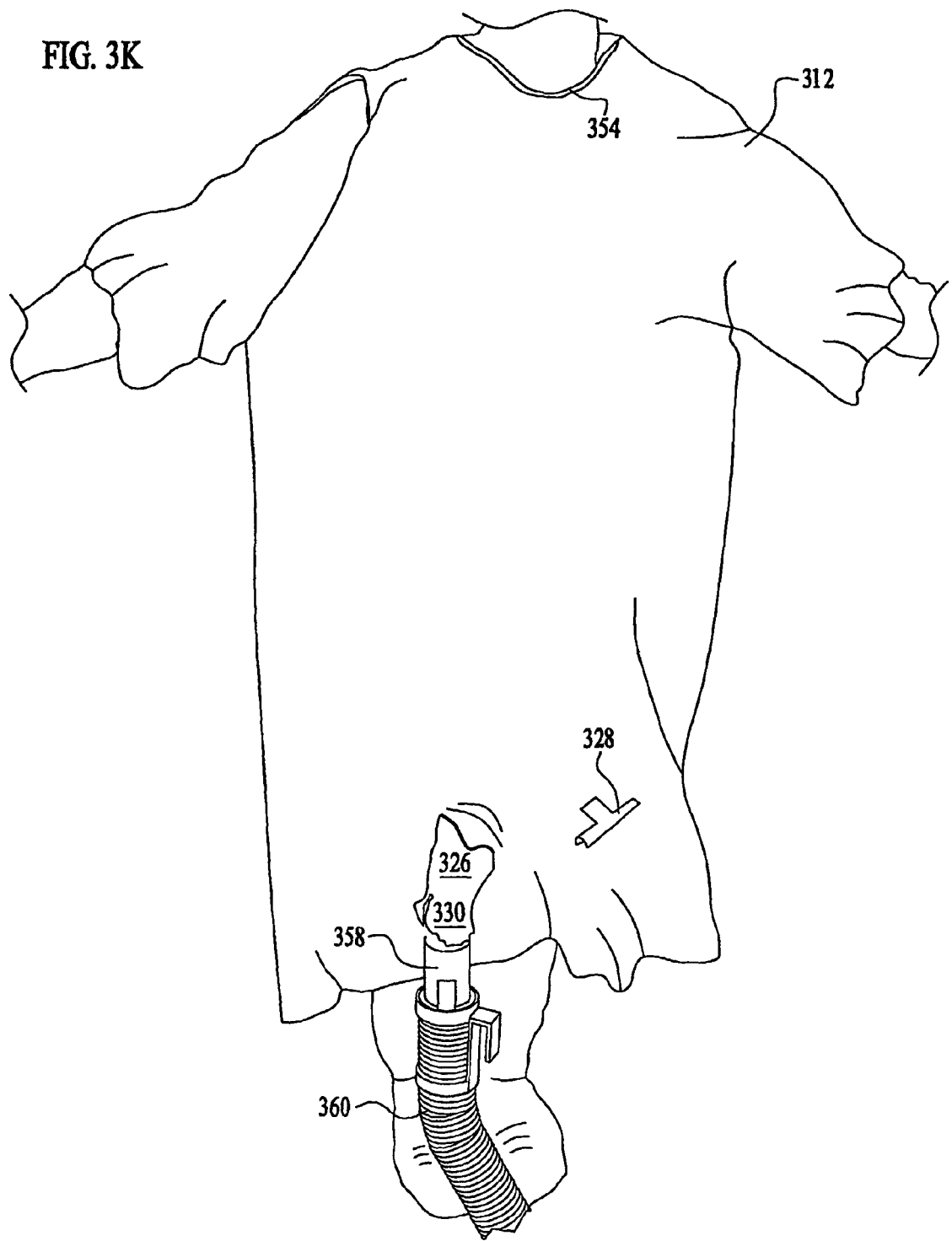

As illustrated in FIGS. 3G, 3I, and 3K, with the device 310 mounted to the gown 312, the seal between the peripheries of the sheets 314, 316 has been breached at the end 330, providing at least one opening through which the end 358 of an air hose 360 may be received to provide a stream of pressurized, thermally treated air directed into the device 310. The at least one opening can also be provided through the end 328. The connection of the end 358 with the end 330 is on the outside of the gown 312, as best seen in FIGS. 3G and 3K. When the stream of pressurized, thermally treated air is provided to the device 310, the device 310 tautens as shown in FIG. 3I, and air is emitted through the sheet 314. As can be appreciated with reference to FIG. 3K, with the gown worn by a person, the device 310, mounted to the gown 312 as described, is disposed so that the permeable sheet 314 faces the person primarily in the region between the person's neck and thighs. Thus when pressurized, thermally treated air is provided to the device 310, it is distributed within the device, and emitted through the sheet 314, focusing or concentrating the emitted air primarily on the person's body core. Convection will then cause heat transfer between the emitted, thermally treated air and the person.

A pneumatic convective device similar to that illustrated in FIGS. 3A-3C is illustrated in FIGS. 3D-3F. In this embodiment, a portion of the inner gown surface 352 is incorporated into the structure of the device 310, serving in the role of the sheet 316 in FIGS. 3A-3C. Otherwise, the structure and operation of the device 310 are as already described.

Alternatively, the device shown in FIGS. 3D-3F could be constructed with an impermeable sheet on the outside of the gown 312, wherein the portion of the gown 312 that includes the inner gown surface 352 would serve as the permeable sheet. Also, in the case of a gown opening in the front, the pneumatic convective device of these figures could be adapted for mounting to the back of the gown.

Refer to FIGS. 3C and 3F for an understanding of how each of the embodiments shown in FIGS. 3A and 3D may be constructed. The sheets 314 and 316 may have an identical laminate structure in which a layer (314a, 316a) of extruded synthetic material is lined with a layer (314b, 316b) of non-woven material. If a laminate structure is selected, holes or apertures 332 are formed through both layers 314a, 314b of the sheet 314. In FIG. 3C, the sheets 314 and 316 are oriented to have the extruded layers (314a and 316a) facing, and the seals 318, 320 are formed by a gluing process or by a heating or ultrasonic process acting through one of the layers of non-woven material. In FIG. 3F, the sheet 314 may be a laminate structure as described above. The gown 312 is a woven cloth, such as cotton, or a non-woven such as spunbond-meltblown-spunbond material (SMS), and the seals between the portion of its inside surface 352 and the extruded layer of the laminate sheet may be formed by a gluing, a heating, or an ultrasonic process. Examples of non-woven material include any one or of polyester, cotton, rayon, polypropylene, and wood pulp. Examples of extruded synthetic material include polypropylene, polyesters, and polyurethanes. Examples of attachment materials and mechanisms by which the device 310 as presented in FIG. 3A can be attached to the gown 312 include two-sided adhesive, hook and loop, sewing, snaps, heat, ultrasonic, rivets, and any and all equivalents thereof.

Figure 4A:
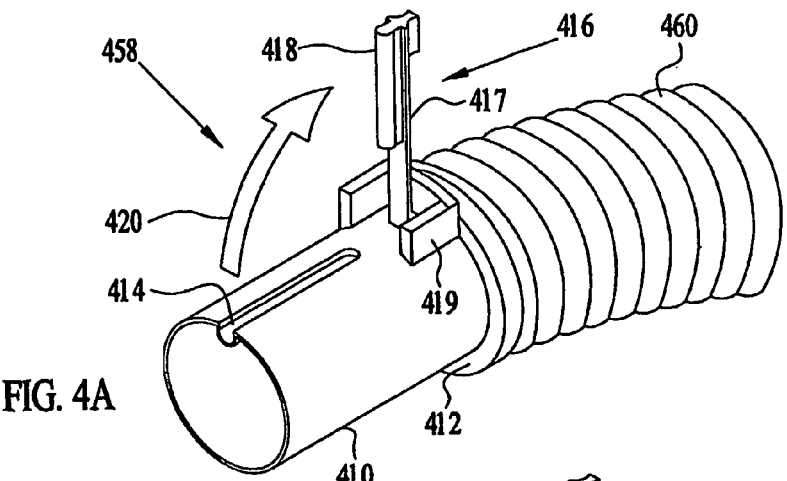
FIGS. 4A-4C illustrate an air hose coupling adapted for use with the pneumatic, convective device of FIGS. 3A-3G.
Figure 4B:
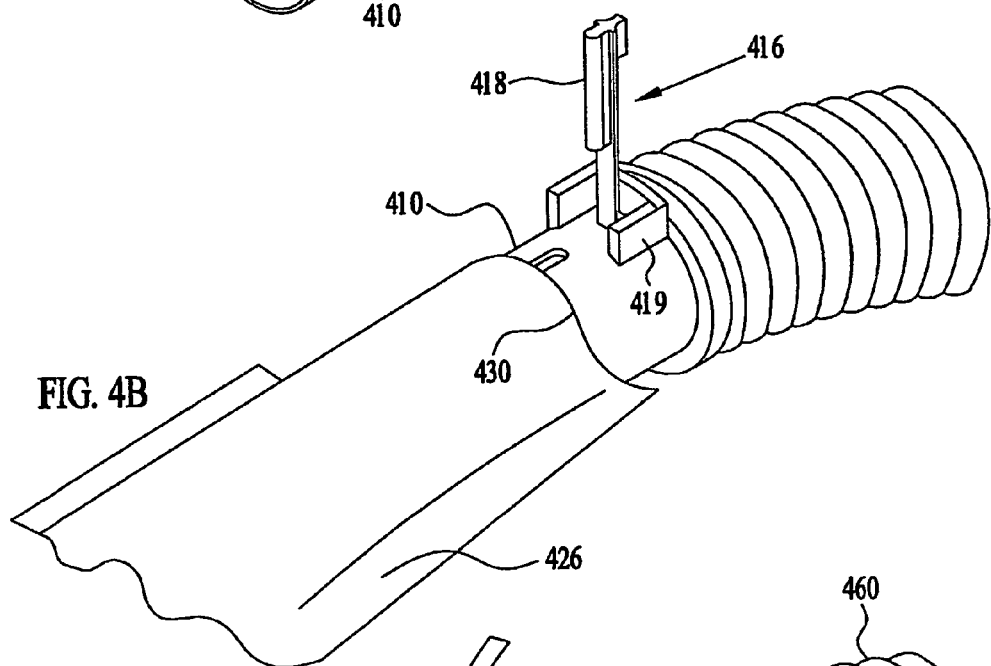
Figure 4C:
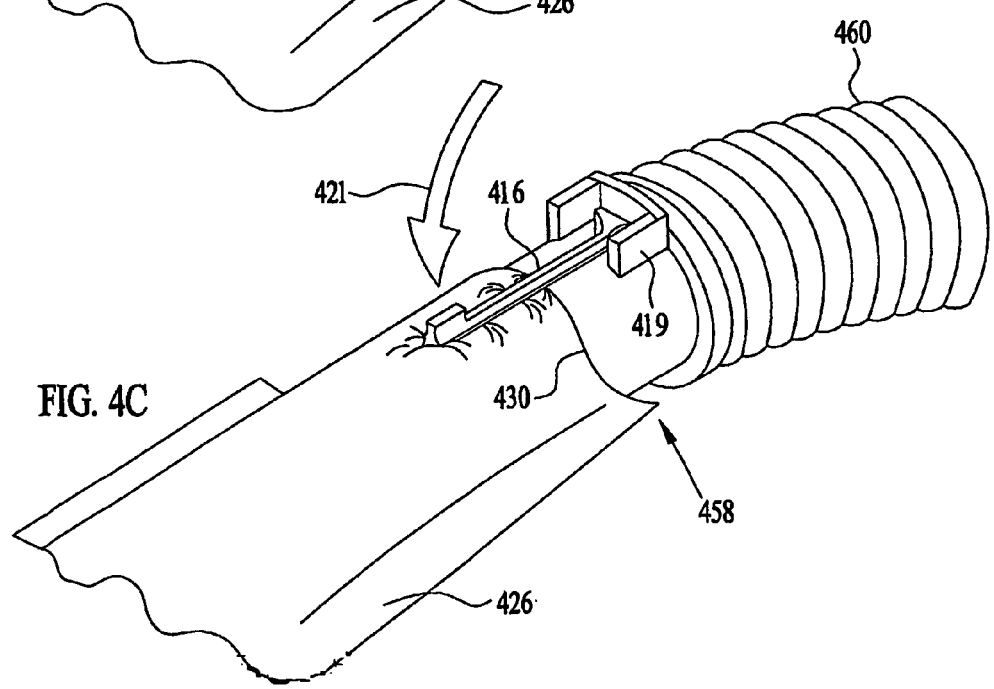

In FIGS. 4A-4C, the air hose 460 has an end 458, which is in the form of a nozzle 410 attached to the air hose 460 at an annular junction 412. The nozzle 410 may be cylindrical or frusto-conical in shape. It is desirable that the nozzle 410 be provided with a mechanism to releasably couple it with a sleeve of one of the pneumatic convective devices of FIGS. 3A-3F and 6A-6I. An example of such a mechanism is shown in these figures. In this example, the nozzle 410 has an elongate longitudinal groove 414. A latch 416 is mounted to the nozzle 410 on a pivot pin 419. The latch 416 is able to pivot on the pin 419 toward and away from the groove 414. The latch 416 has a bar 418 that may be snapped into the groove 414 to retain the latch in a latching engagement with the groove 414. The latch may be pulled away from the groove 414 to unsnap the bar 418 therefrom. The snapping engagement of the bar 418 and the groove 414 permits the sleeve formed in the projection 426 (or in the Y stem 620 shown in FIGS. 6A-6I) to be held by or to the nozzle 410 in a releasably coupled engagement therewith while a stream of pressurized, thermally treated air is provided to the pneumatic convective device of which the sleeve is an element. The sleeve and nozzle may be decoupled and separated when the bar 418 is unsnapped from the groove 414.

Preferably, the diameter of the sleeve is larger than that of the nozzle to allow for easy entry of the nozzle. As the latch is engaged, it gathers the excess material of the sleeve, and pulls it into the groove, thus securing the fit to reduce or eliminate air leakage where the sleeve and the nozzle are joined. The nozzle may also be configured to swivel to accommodate the diverse range of motion the devices will experience in various settings.

The respective parts of the air hose end shown in FIGS. 4A-4C may be molded from plastic, assembled by bonding, and then attached to the end of an air hose by conventional means.

Figure 5A:
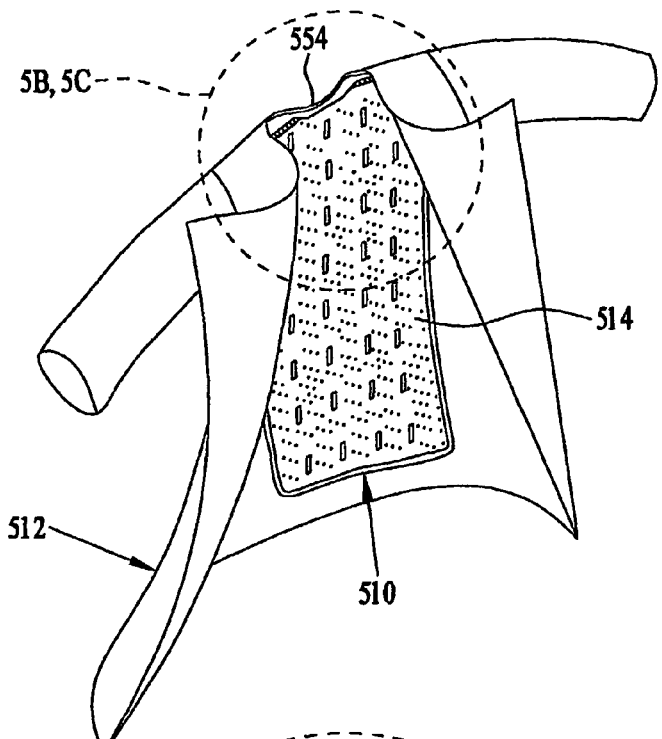
FIGS. 5A-5C illustrate complementary adaptations of an end of an air hose and an edge of a pneumatic convective device according to FIG. 3A.
Figure 5B:
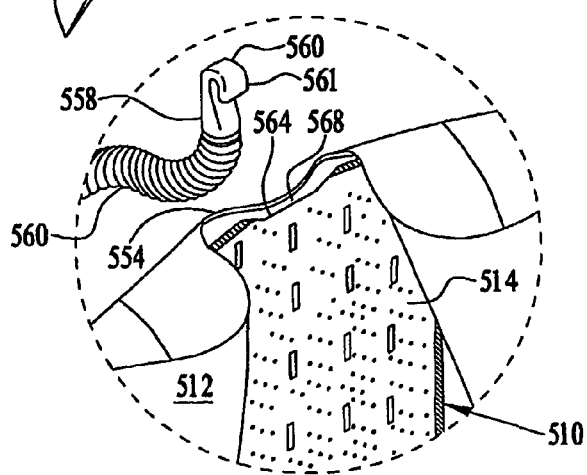
Figure 5C:
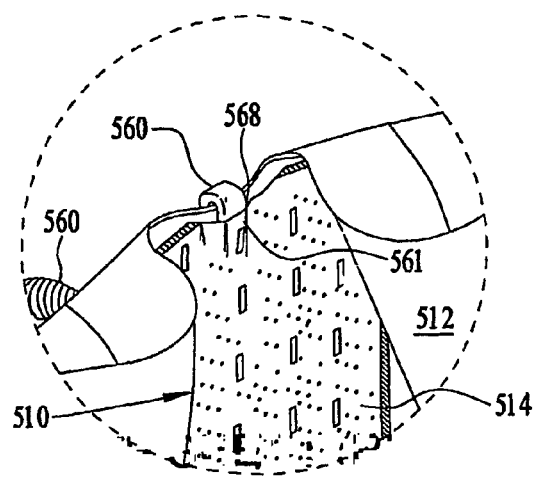

FIGS. 5A-5C illustrate complementary adaptations of a pneumatic convective device according to FIG. 3A-3F and the end of an air hose. In these figures, a pneumatic convective device 510, with or without projections, and without an indentation, is disposed on a gown 512, with the permeable sheet 14 facing inwardly of the gown 512. An opening 568 into the pneumatic structure is provided between the upper edge 554 of the gown 512 and the upper edge 568 of the sheet 514. This opening 568 provides air flow access into the pneumatic structure. The air hose 560 has a crooked end 558 with a bent portion 560, the end 561 of which may be received in the opening 568, with the inner part of the bent portion 560 supported on the upper edge 554 of the gown 512. In operation, a stream of pressurized, thermally treated air flows through the hose 560, into the crooked end 558, the bent portion 560, and the end 561 into the pneumatic convective device 510. The air hose end 558 may be molded from plastic.

Figure 6A:
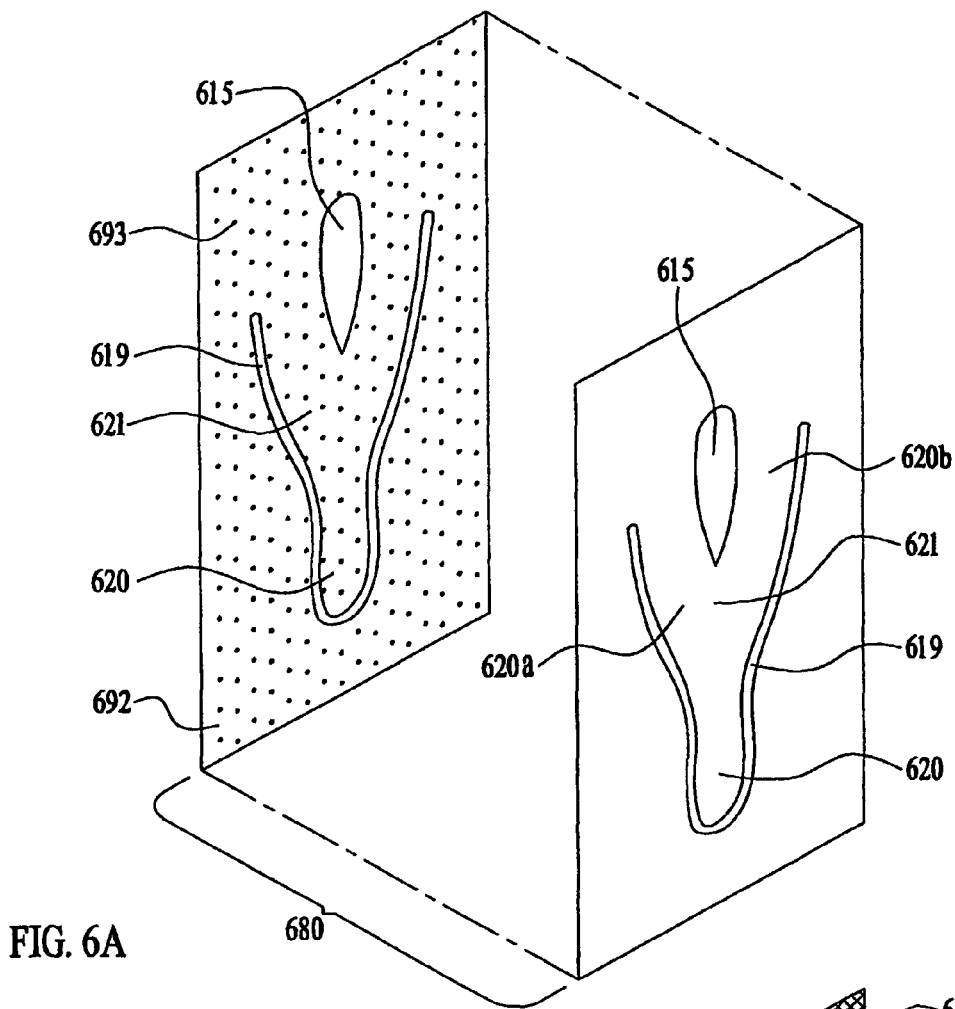
Figure 6B:
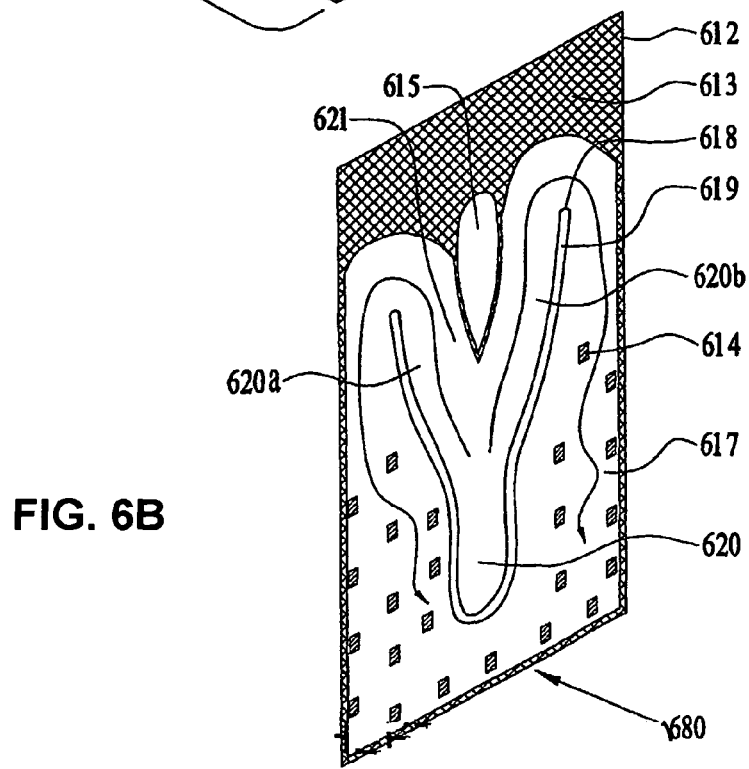
Figure 6E:
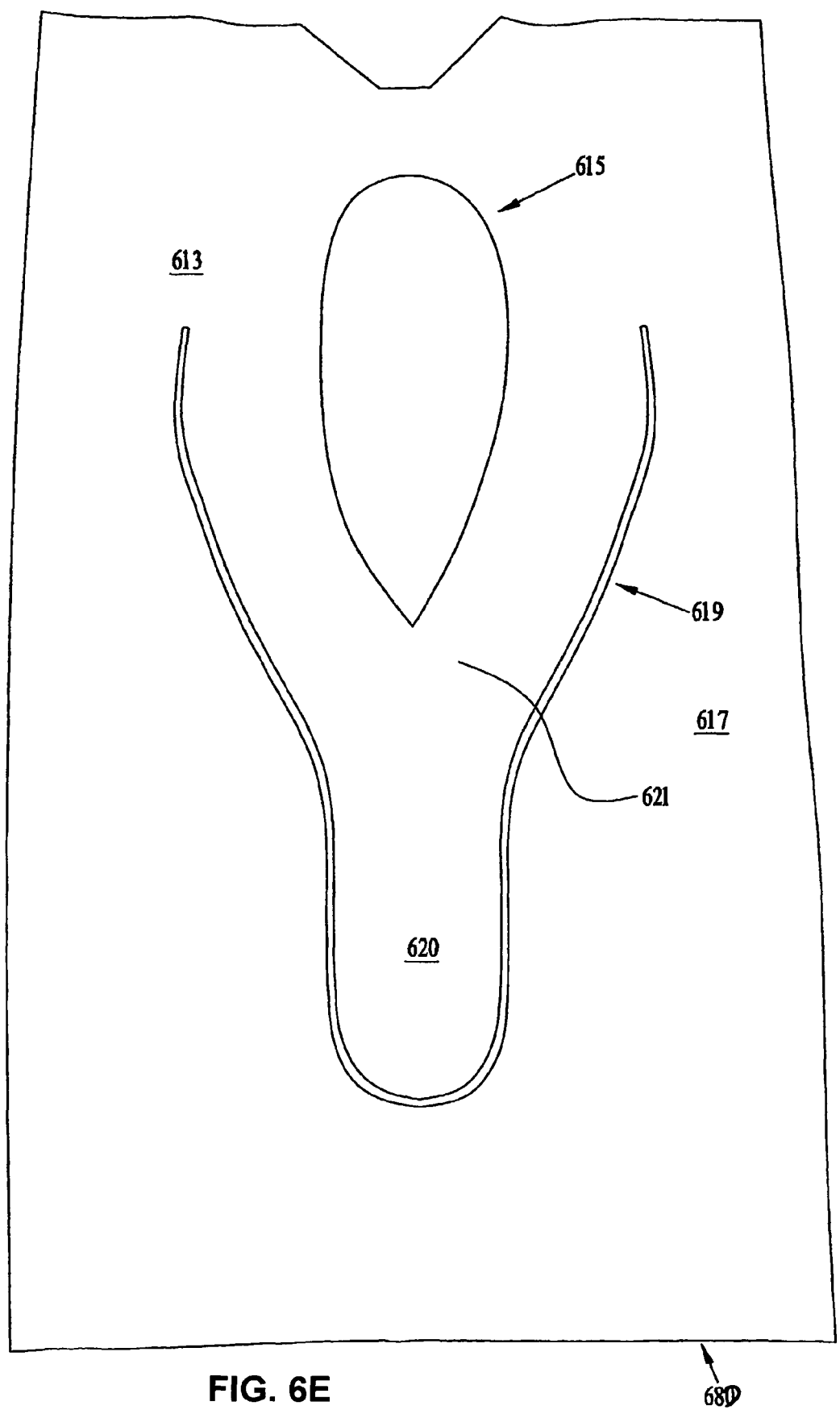
FIG. 6E is a plan view photograph of the pneumatic convective device of FIG. 6A-6D.

FIGS. 6A-6I illustrate another exemplary pneumatic convective device which embodies the invention. FIGS. 6A, 6B and 6D illustrate the device 680, after it has been fabricated, with FIG. 6A showing an exploded view of the device and FIG. 6B showing an assembled view of the device. The pneumatic convective device 680 may be made by joining two sheets of material 690 and 692. Preferably, at least one of the sheets 690 and 692 is permeable to air; in this example, the sheet 692 is air-permeable, this being represented by apertures 693 that open through the sheet 692. The two sheets 690 and 692 are sealed together continuously at their respective peripheries 612, in a non-inflatable region 613 extending inwardly from one edge in the direction of an opposing edge, and intermittently at a plurality of locations 614 in a distribution region 617 bounded by the non-inflatable region 613, the opposing edge, and the sides of the sheets 690 and 692. An opening 615 is provided through the two sheets 690 and 692 in the non-inflatable region 613. A generally Y-shaped contoured opening 619 is provided through both sheets 690 and 692 in the region 617. The region 617 is sealed from the opening 619 by the continuous seal 618. As thus constructed, the device 680 includes the non-inflatable region 613, the region 617, and a Y-shaped region 621 defined by the contoured opening 619. The Y-shaped region has a stem 620 and transitions to two branches 620a and 620b through which it communicates with the distribution region 617.

Figure 6F:
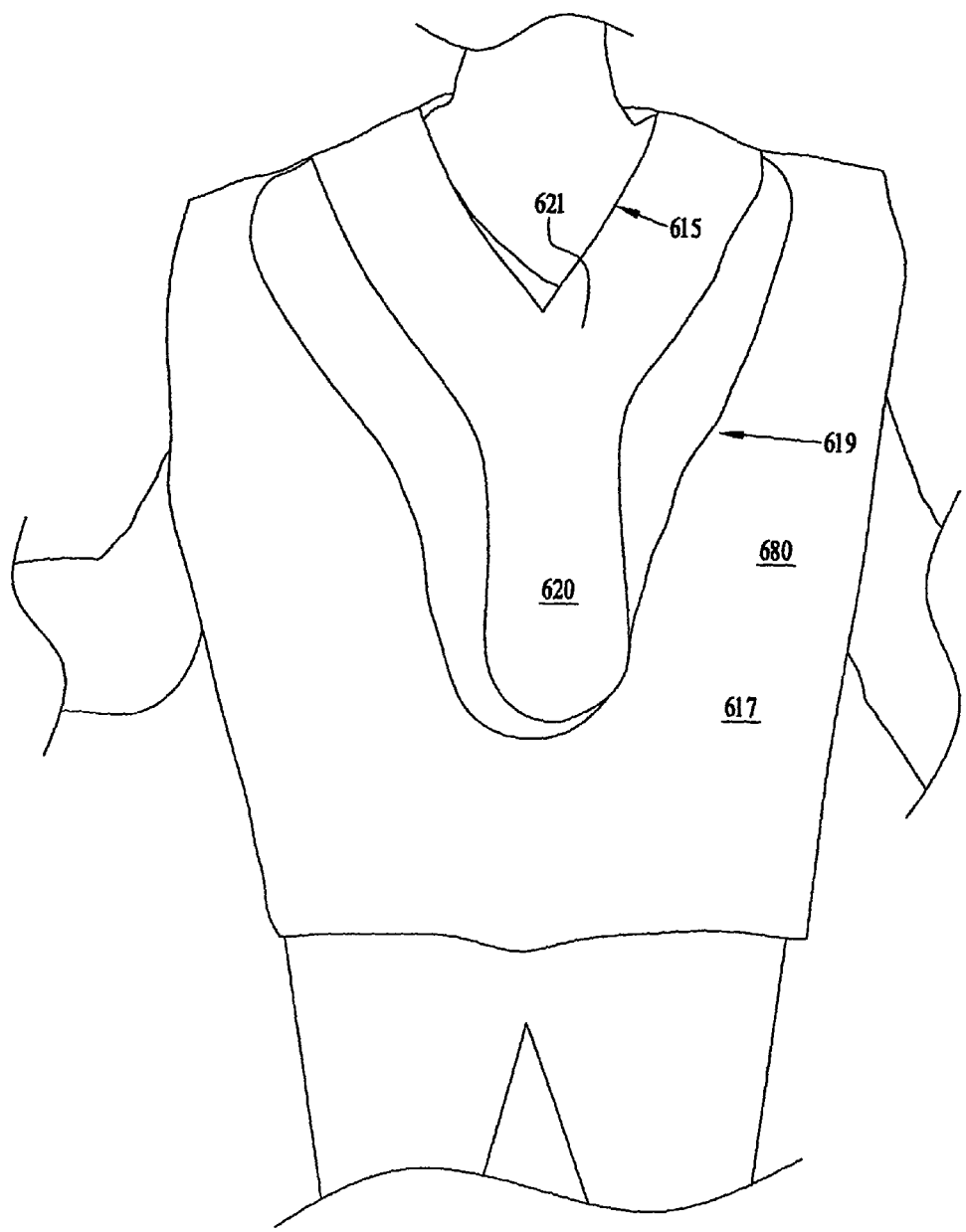
FIG. 6F is a photograph of the pneumatic convective device disposed, uninflated on the shoulders of a user.

FIGS. 6C and 6F show the device 680 deployed for use. As illustrated, the opening 615 receives the head of a user so that the device 680 is disposed on the neck and shoulders of the user much like a Mae West life jacket, with the sheet 692 facing toward, and the sheet 690 away from, the user. In this disposition, the non-inflatable region 613 hangs over the user's shoulders, toward the user's back, while the distribution region 617 and the Y-shaped region 621 are disposed adjacent, or near to the user's chest, with the stem 620 pointing toward the user's waist. FIG. 6H shows the hospital gown received over the device 680, so that the distribution region 617 is disposed between the user and the gown 612, with the Y-shaped region 621 extending over the edge 654 and disposed on the outside of the gown 612.

Figure 6G:
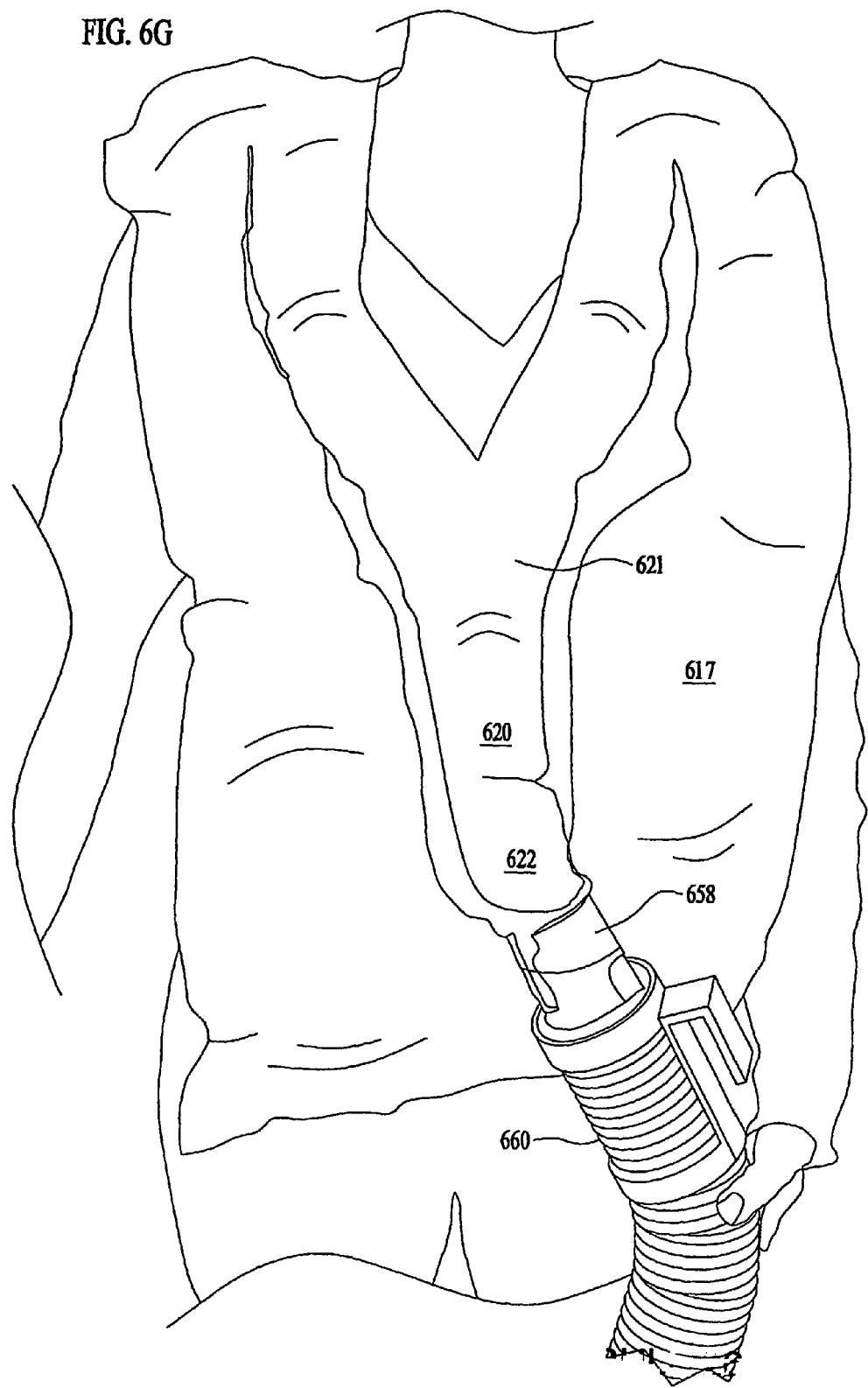
FIGS. 6G-6I are photographs showing the pneumatic convective device of FIGS. 6A-6D in use.
Figure 6H:
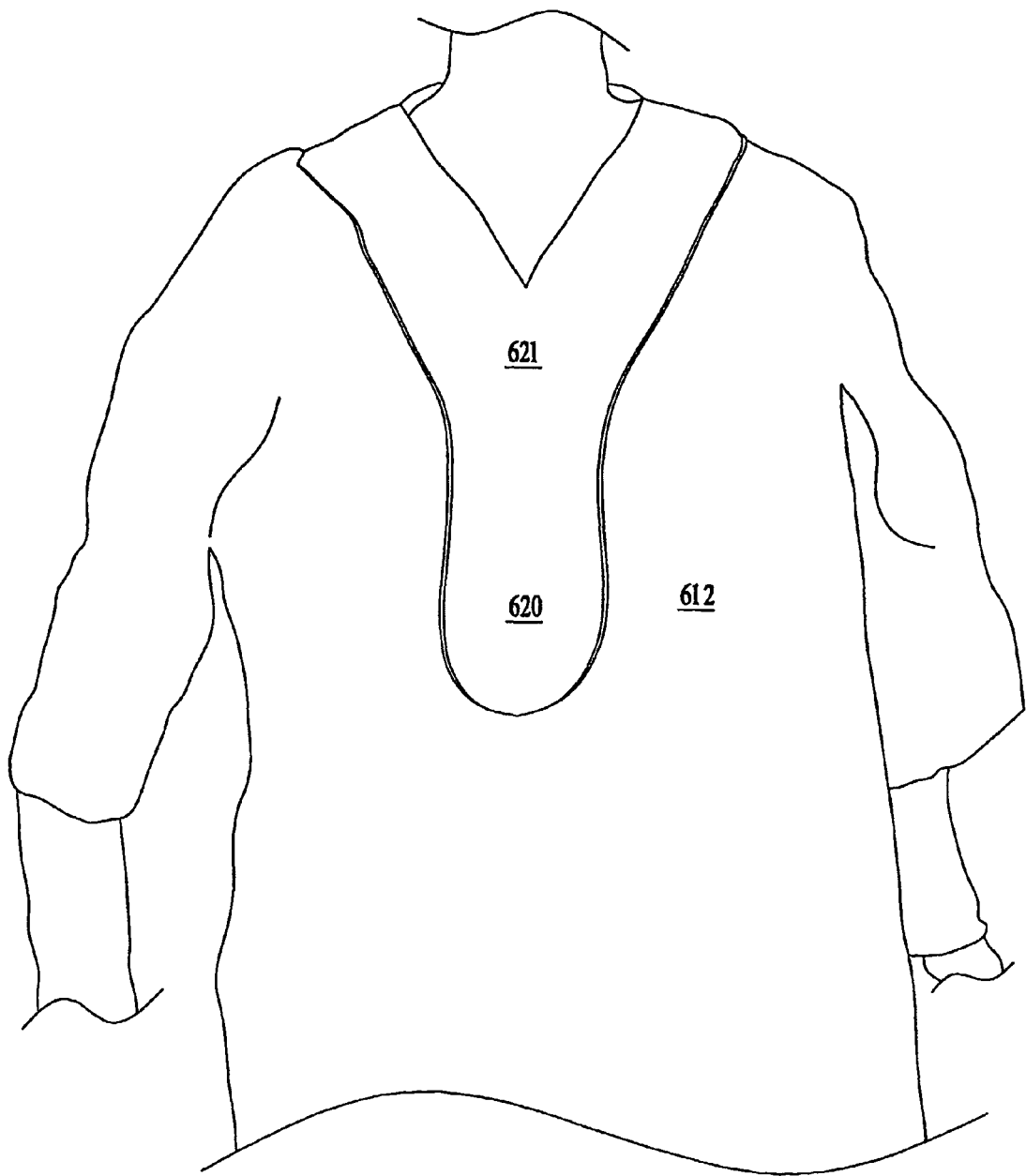

In FIG. 6C, the end 622 of the stem 620 is opened; in FIG. 6G, the end 658 of the air hose 660 is received in the opened end 622 and provides a stream of pressurized, thermally-conditioned air. The pressurized air flows through the stem 620 into the branches 620a and 620b of the Y-shaped region 621 whence it is distributed through and inflates the pneumatic structure of the distribution region 617. The air is emitted from the distribution region 617 through the permeable sheet 692 toward the body core of the user. The figure shows the inflatable, comfortable hose connection portion of the device to be at the neck area, however it should be noted that it could be alternatively be located at the arm, back, shoulder or lower hem areas.

Figure 6I:
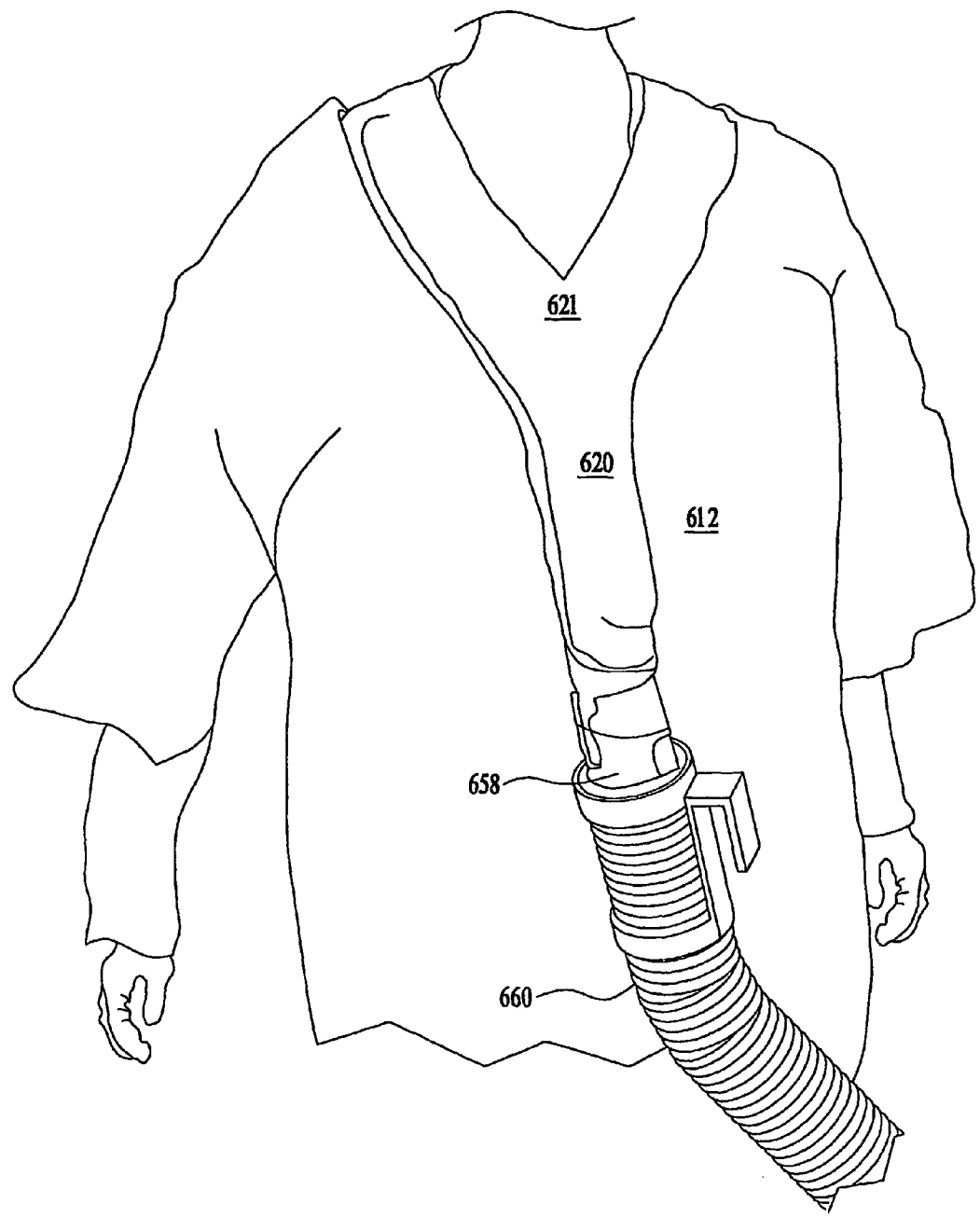

Refer now to FIGS. 6D and 6I. When the device 680 is disposed with respect to the gown 612 as shown in FIG. 6H and pressurized air is provided as in FIG. 6G, the air is distributed through the regions 621 and 617 and is emitted toward the body core of the user through the permeable sheet 692.

The sheet 692 may have the structure described above for the sheet 614, while the sheet 690 may have the structure described above for the sheet 616.

One advantage of the embodiments thus far disclosed is that the pneumatic convective devices may be provided to the user in bulk fashion, such as on a roll or in a dispenser box. For example, the devices provided on a roll dispenser may have perforated lines separating each device. Users may simply select a new device for application in the field, say in the patient's dressing room or at the patient's care site. Further, as in the case of the embodiment shown in FIG. 3A, the patient or clinician may select the pneumatic device from a roll and insert it into a gown as desired. In this way the gowns may be laundered and reused and each pneumatic device disposed of after use. This roll dispenser will allow for more cost-effective inventory storage and ease of accessibility.

Figure 7A:
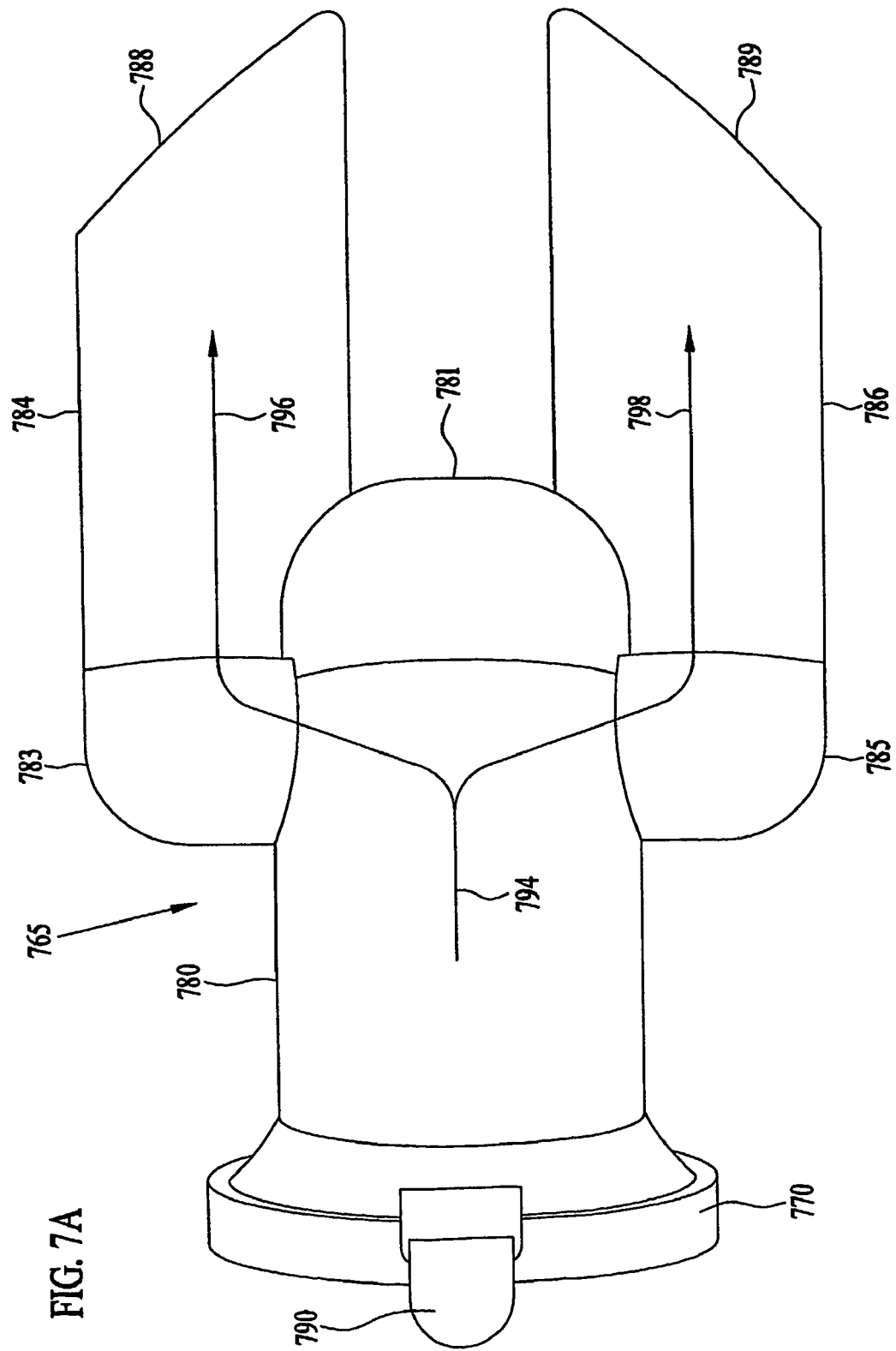
FIGS. 7A-7F illustrate complementary adaptations of an end of an air hose and a stem of a pneumatic convective device according to FIG. 6A.
Figure 7B:
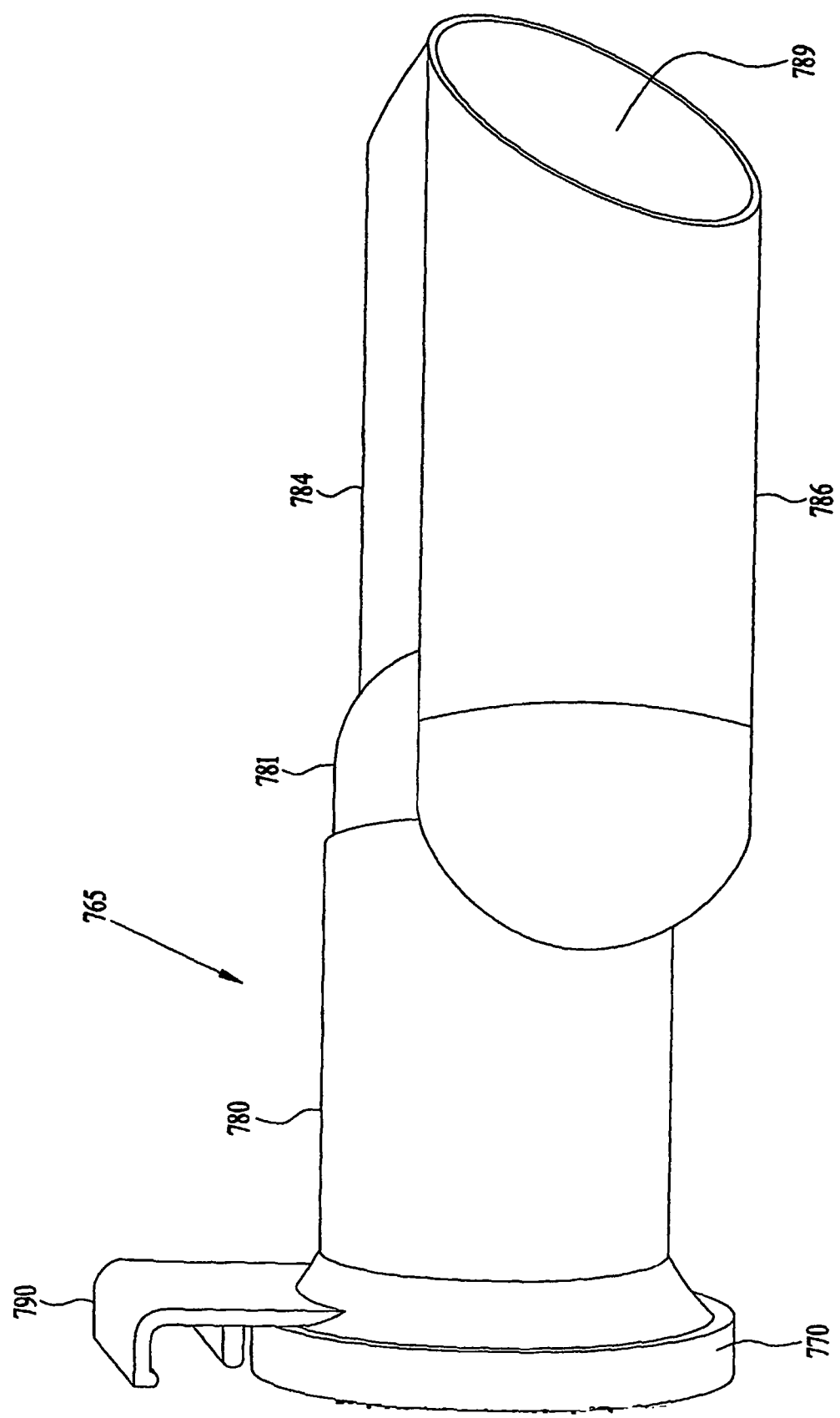
Figure 7C:
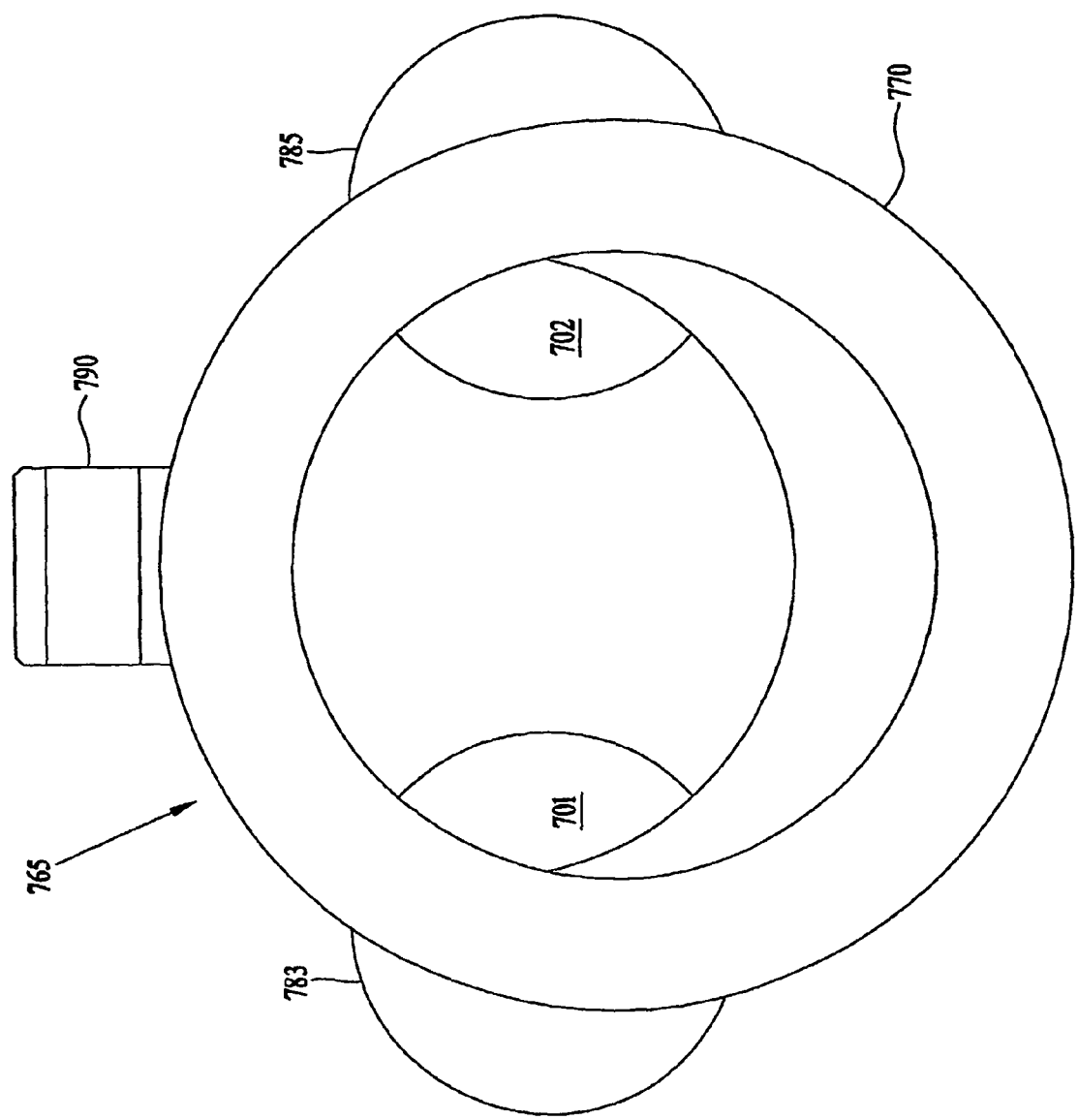
Figure 7E:
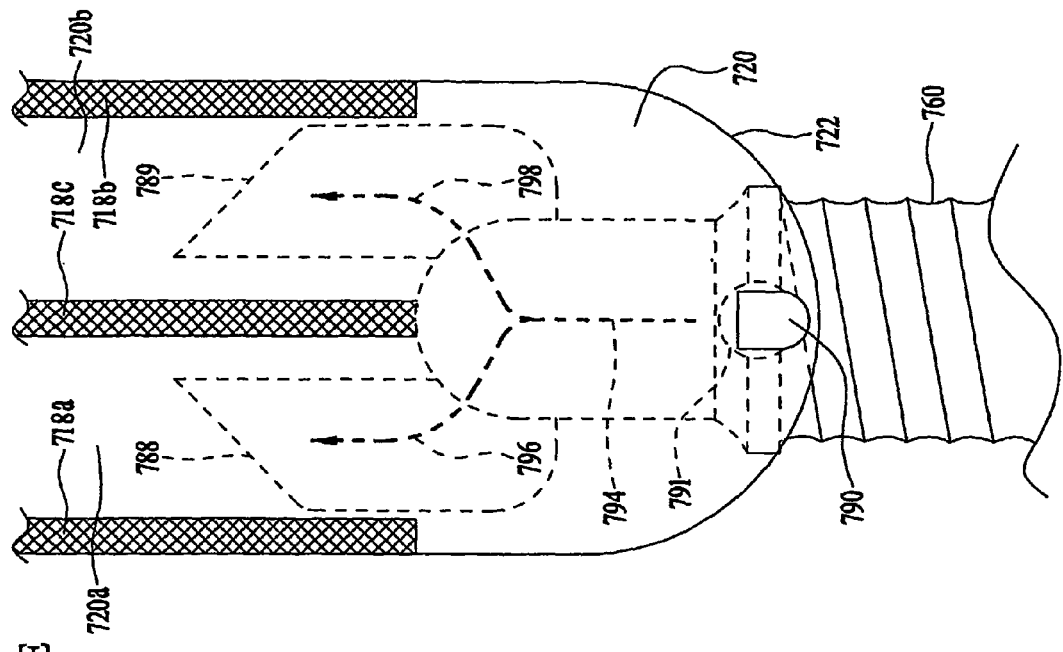
Figure 7D:
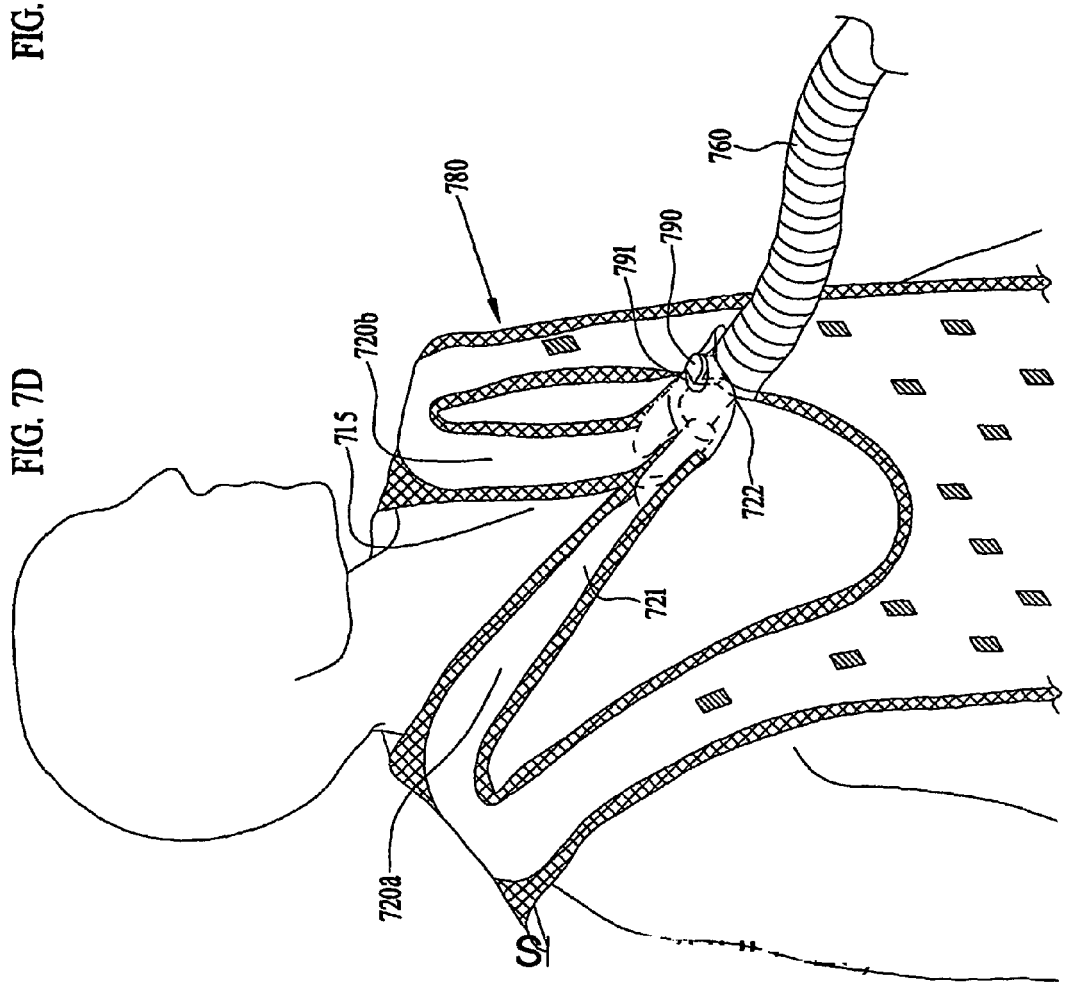
Figure 7F:
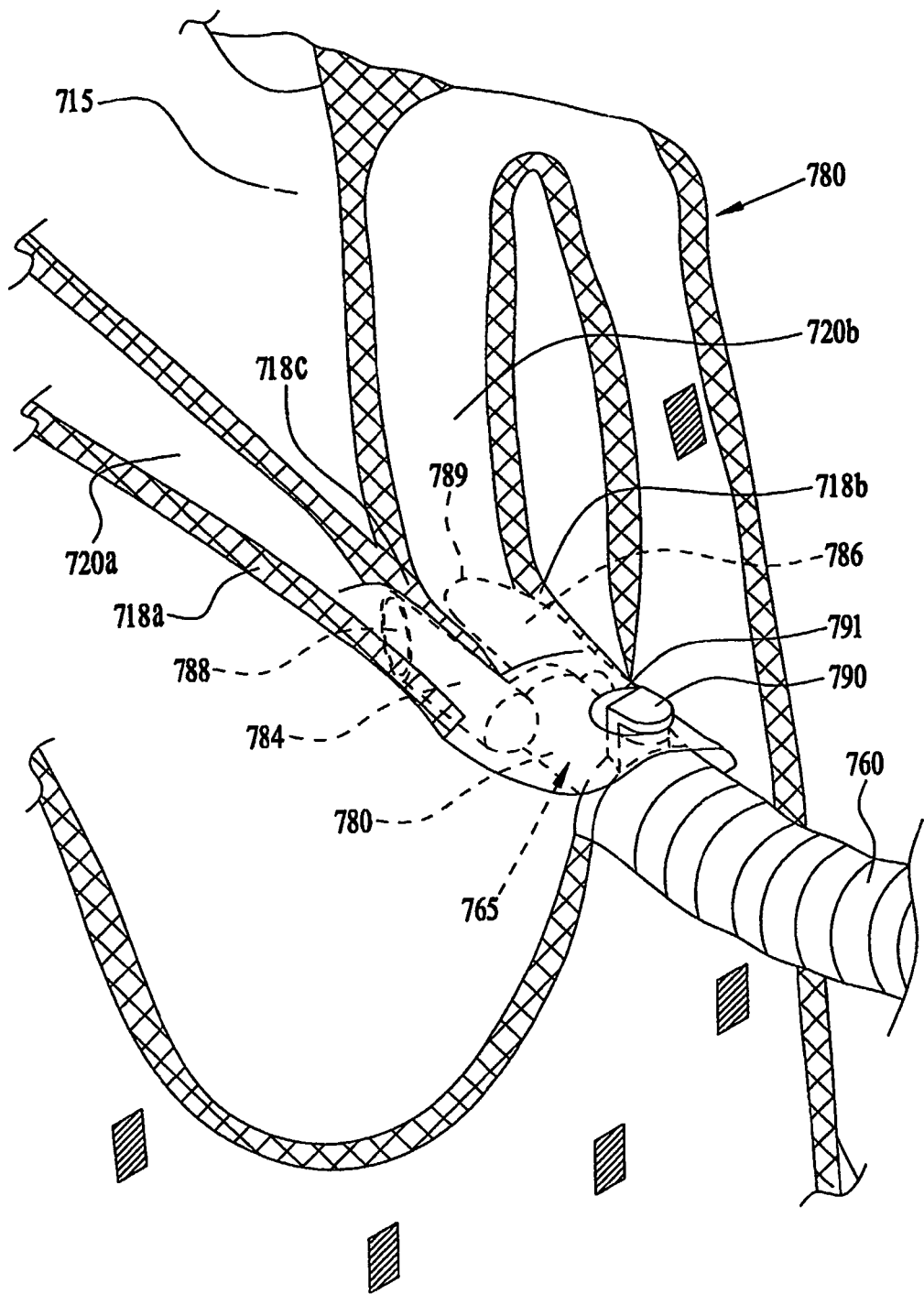

FIGS. 7A-7F illustrate complementary adaptations of a pneumatic convective device according to FIG. 6A-6C and the end of an air hose. In the pneumatic convective device 780 which is shown in FIG. 7D, the stem 720 is shortened, and the seal 718 terminates in an open configuration near the end 722, which is defined by two spaced-apart ends 718a and 718b of the seal 718. As best seen in FIGS. 7E and 7F, a third seal 718c between the sheets 790 and 792 is disposed between the ends 718a and 718b, and extends from the opening 715 toward the end 722. These seals divide the stem 720 into the respective branches 720a and 720b of the Y-shaped region 721. Each branch is in communication with the distribution region 717. A nozzle 765 formed as a manifold is adapted to be received in the end 722 and to provide a plurality of separate streams of pressurized, thermally treated air into the device 780. The nozzle 765 has a plenum 780, and two further plenums 784 and 786 that are in communication with the plenum 780. The manifold nature of the nozzle lies in its ability to accept a stream of pressurized, thermally treated air through the plenum 780 and to split or divide the stream into two streams of pressurized, thermally treated air such that each of the streams is provided to a respective one of the branches 720a and 720b. The specific nozzle construction that is shown in these figures is meant to be illustrative of but one embodiment of a manifold nozzle, it being understood that other equivalent constructions will occur to the skilled artisan who is put in possession of these teachings.

Each of the plenums is illustrated in FIGS. 7A-7C as a cylindrical section; although this is a preferred shape, it is not the only one that can be used. The plenum 780 has a connecting ring 770 mounted at one of its ends for seating on the end of an air hose. A cap 781 closes the other end of the plenum 780. One end of the plenum 784 has a cap 783 mounted to it; the other end 785 is open and in the shape of an offset point. Similarly, one end of the plenum 786 has a cap 785 mounted to it; the other end 789 is open and in the shape of an offset point. The plenum 784 is mounted, joined to, or formed integrally with the plenum 780 near the cap 781 such that the cap 783 adjoins and partially overlaps the cap 781. Similarly, the plenum 786 is mounted, joined to, or formed integrally with the plenum 780 near the cap 781 such that the cap 785 adjoins and partially overlaps the cap 781. As best seen in FIG. 7C, the nozzle 765 opens from the connecting ring 770, through the plenum 780, to, through and out the respective ends of each of the plenums 784, 786. As shown schematically in FIGS. 7A and 7E, this construction divides an input stream of air 794 into two streams 796 and 798.

The manifold nozzle 765 is received in the stem 720 through the end 722, with the plenum ends 788 and 789 positioned in the branches 720a and 720b, respectively. The manifold nozzle 765 is retained in this position by a pommel 790 which engages an opening 791 formed in the stem 720. Thus disposed, the manifold nozzle 765 provides a stream of air to the Y-shaped portion 721 of the pneumatic convective device 780 by way of the plenum 780, which is adapted by the connecting ring 770 for seating on the end of an air hose to receive a stream of pressurized air from the air hose. The two plenums 784 and 786 are disposed against the plenum 780 in a spaced-apart array corresponding to branches 720a and 720b of the Y-shaped portion 721. In this regard, the spaced-apart array illustrated has the two plenums 784 and 786 disposed in parallel at diametrically opposed locations on respective sides of the plenum 780. This is not meant to constrain the spaced apart array to just such a configuration. Indeed, the plenums 784 and 786 may be disposed to diverge at an angle such as an angle at which the branches 720a and 720b diverge in the Y-shaped region 720. Each of the two plenums 784 and 786 has an opening in communication with the plenum 780 for emitting a respective stream of pressurized air into a respective branch of the Y-shaped region in response to the stream of pressurized air received by the plenum 780.

The manifold nozzle may be assembled by joining separate pieces, each molded from plastic, or the entire nozzle may be molded from plastic as a unitary device and mounted conventionally to an end of an air hose.

In a case where an air hose is coupled to a pneumatic convective device through the end of a projection, such as in the first two sets of FIGS. (3A-3F and 6A-6I) the projection is typically in the form of a sleeve. This can be seen clearly in FIGS. 3G and 6D. In such cases, the air hose end must be adapted for use with a sleeve. An objective of such use would be to releasably couple the air hose end to the sleeve in such a manner that the air hose end remains disposed within the sleeve in order to deliver a stream of pressurized, thermally treated air into the pneumatic convective device while the device is in use, while providing the ability to be simply decoupled or released from the sleeve when the use is ended. One example of a mechanism that meets this objective is illustrated in FIGS. 4A-4C.

The embodiments that are illustrated and described above are meant to be representative, and not limiting, of our invention. Other variations and embodiments will be apparent to those skilled in the art upon reading this description. For example, the illustrations and description show a pneumatic convective device disposed on or at the front of a clinical garment for convectively warming the chest of a person. The pneumatic convective device could also be mounted to or disposed at the back or sides of the garment, or may be adapted, sized, or constructed to extend along more or less of the thorax than shown in the illustrated embodiments of this invention.

What is claimed is:

1. A mechanism for releasably coupling an end of an air hose to a sleeve of a pneumatic convective device, comprising:
   a nozzle;
   a groove in the nozzle;
   a latch for pivoting toward and away from the groove; and
   a bar on the latch for releasably engaging the groove.

\* \* \* \* \*

UNITED STATES PATENT AND TRADEMARK OFFICE
CERTIFICATE OF CORRECTION

| | | |
|---|---|---|
| PATENT NO. | : 7,837,721 B2 | Page 1 of 4 |
| APPLICATION NO. | : 10/508319 | |
| DATED | : November 23, 2010 | |
| INVENTOR(S) | : Scott Douglas Augustine | |

It is certified that error appears in the above-identified patent and that said Letters Patent is hereby corrected as shown below:

Title Page
Delete Title page and replace with new Title page, (attached)
Item [73], Assignee, delete "Prarie," and insert -- Prairie, --, therefor.

Drawings
In the drawings, original sheet 3/30 containing Fig. 1D is missing, insert the attached page, therefor.

Column 3
Line 2, delete "Warming" and insert -- "Warming --, therefor.
Line 4, delete "Device," and insert -- Device", --, therefor.

Column 6
Line 26, delete "FIG." and insert -- FIGS. --, therefor.

Column 7
Line 50, after "to" delete "so".

Column 8
Line 12, delete "grow" and insert -- gown --, therefor.
Line 15, after "with" insert -- the --.
Line 37, delete "1161b)" and insert -- 116b) --, therefor.

Column 9
Line 4, after "or" insert -- any --.
Line 8, after "may" insert -- be --.
Line 19, delete "WRMING" and insert -- WARMING --, therefor.
Line 25, delete "connective" and insert -- convective --, therefor.

Signed and Sealed this
Eleventh Day of September, 2012

David J. Kappos
*Director of the United States Patent and Trademark Office*

CERTIFICATE OF CORRECTION (continued)
U.S. Pat. No. 7,837,721 B2

Column 11
Line 11, after "to" delete "so".

Column 13
Line 14, delete "FIG." and insert -- FIGS. --, therefor.

Column 14
Line 16, delete "6I. When" and insert -- 6I, when --, therefor.
Line 39, delete "FIG." and insert -- FIGS. --, therefor.

(12) United States Patent
Augustine et al.

(10) Patent No.: US 7,837,721 B2
(45) Date of Patent: Nov. 23, 2010

(54) PATIENT COMFORT APPARATUS AND SYSTEM

(75) Inventors: Scott D. Augustine, Bloomington, MN (US); Thomas Peter Anderson, Savage, MN (US); Randall Charles Arnold, Minnetonka, MN (US)

(73) Assignee: Arizant Healthcare Inc., Eden Prarie, MN (US)

( * ) Notice: Subject to any disclaimer, the term of this patent is extended or adjusted under 35 U.S.C. 154(b) by 1427 days.

(21) Appl. No.: 10/508,319

(22) PCT Filed: Apr. 10, 2003

(86) PCT No.: PCT/US03/11128

§ 371 (c)(1),
(2), (4) Date: Mar. 3, 2005

(87) PCT Pub. No.: WO03/086500

PCT Pub. Date: Oct. 23, 2003

(65) Prior Publication Data

US 2005/0143796 A1 Jun. 30, 2005

Related U.S. Application Data

(60) Provisional application No. 60/371,314, filed on Apr. 10, 2002.

(51) Int. Cl.
*A61F 7/00* (2006.01)
(52) U.S. Cl. .................. 607/96; 607/104; 607/107
(58) Field of Classification Search .............. 607/96, 607/104, 107, 108; 2/81, 102, 114; 5/423, 5/347
See application file for complete search history.

(56) References Cited

U.S. PATENT DOCUMENTS

| | | | |
|---|---|---|---|
| 2,512,559 A | 6/1950 | Williams | 5/347 |
| 2,573,414 A | 10/1951 | Dunn | 128/144 |
| 2,826,758 A | 3/1958 | Kahn | 2/81 |
| 3,468,299 A * | 9/1969 | Amato | 126/204 |
| 3,610,323 A | 10/1971 | Troyer | 165/46 |
| 3,757,366 A * | 9/1973 | Sacher | 5/423 |

(Continued)

FOREIGN PATENT DOCUMENTS

FR 821150 11/1937

(Continued)

OTHER PUBLICATIONS

Written Opinion of the International Search Authority (EPO) in PCT/US2006/041028, mailed Feb. 20, 2007.
International Search Report and Written Opinion in PCT/US2006/004644, mailed Dec. 18, 2006.

(Continued)

*Primary Examiner*—Roy D Gibson
(74) *Attorney, Agent, or Firm*—Terrance A. Meador; INCAPLAW

(57) ABSTRACT

Apparatus and a system for thermally comforting a patient include pneumatic, convective providing thermal treatment for persons or animals, which is adapted for use in combination with a clinical garment such as a hospital gown, robe, bib, and other equivalents. The pneumatic convective device provides convective warming focused or directly primarily on the thorax or body core. The pneumatic convective device includes at least one inlet for being accessed through a clinical garment, a region in distribution with the inlet for distributing a stream of pressurized, thermally treated air, and a permeable member for emitting pressurized, thermally treated air from the distribution region.

1 Claim, 30 Drawing sheets